US009808400B2

(12) United States Patent
Tomes et al.

(10) Patent No.: US 9,808,400 B2
(45) Date of Patent: *Nov. 7, 2017

(54) CATHETER TRAY, PACKAGING SYSTEM, AND ASSOCIATED METHODS

(71) Applicant: Medline Industries, Inc., Mundelein, IL (US)

(72) Inventors: Jennifer E. Tomes, Mundelein, IL (US); Deborah B. Adler, New York, NY (US); Jack E. Maze, Long Grove, IL (US); Alberto C. Savage, Buffalo Grove, IL (US); Kenneth S. Chua, Glenview, IL (US); Earl D. Wilson, Ingleside, IL (US); John Henry Kutsch, Harvard, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,909

(22) Filed: Apr. 30, 2014

(65) Prior Publication Data
US 2014/0231287 A1    Aug. 21, 2014

Related U.S. Application Data

(60) Continuation of application No. 12/846,675, filed on Jul. 29, 2010, now Pat. No. 8,746,452, which is a
(Continued)

(51) Int. Cl.
*A61J 1/00*  (2006.01)
*A61M 25/00*  (2006.01)
(Continued)

(52) U.S. Cl.
CPC ............... *A61J 1/00* (2013.01); *A61B 50/30* (2016.02); *A61B 50/33* (2016.02); *A61M 25/00* (2013.01);
(Continued)

(58) Field of Classification Search
USPC ........ 206/570–572, 363–366, 370, 561, 563, 206/557; 220/505, 555
See application file for complete search history.

(56) References Cited

U.S. PATENT DOCUMENTS 2,659,485 A    11/1953    Duley et al.
2,715,296 A    8/1955    Petit
(Continued)

FOREIGN PATENT DOCUMENTS

CN    201823147    5/2011
JP    2007-229520    9/2007
(Continued)

OTHER PUBLICATIONS

"IPR 2015-00514—Request for Rehearing Denied", IPR2015-00514; U.S. Pat. No. 8,678,190; Decision on Request for Rehearing—Denied; Mailed Jul. 16, 2015.
(Continued)

*Primary Examiner* — Robert Poon

(57) ABSTRACT

A tray (100) for accommodating a coiled medical device, such as a catheter assembly (700), includes a first compartment (101), a second compartment (102), and a third compartment (103). The catheter assembly (700) and devices associated with a catheterization procedure, such as syringes (701,702) containing sterile water and lubricating jelly and a specimen container (703) can be disposed within the tray. A first barrier (105) and second barrier (106) separate the compartments. The barriers can have openings (121,122) therein to accommodate large syringes or to enable the first compartment (101) to be used as a lubricant applicator for the catheter. The first compartment (101) can include a stair-stepped contour (115) such that the syringes are held at different depths to facilitate ease of use. The various devices
(Continued)

can be disposed within the tray (100) in accordance with their order of use in the catheterization procedure.

22 Claims, 9 Drawing Sheets

Related U.S. Application Data division of application No. 12/495,148, filed on Jun. 30, 2009, now Pat. No. 8,631,935.

(60) Provisional application No. 61/183,629, filed on Jun. 3, 2009.

(51) Int. Cl.
*A61B 50/33* (2016.01)
*A61B 50/30* (2016.01)
*A61B 42/00* (2016.01)
*A61B 46/00* (2016.01)

(52) U.S. Cl.
CPC ........... *A61M 25/002* (2013.01); *A61B 42/00* (2016.02); *A61B 46/00* (2016.02); *A61B 2050/3008* (2016.02); *A61B 2050/3015* (2016.02)

(56) References Cited

U.S. PATENT DOCUMENTS

| | | |
|---|---|---|
| 2,781,611 A | 2/1957 | West |
| 2,886,316 A | 5/1959 | Ayala |
| 2,947,415 A | 8/1960 | Garth |
| 2,954,642 A | 10/1960 | Roderick |
| 2,959,891 A | 11/1960 | Barnett et al. |
| 3,107,786 A | 10/1963 | Adelman |
| 3,166,189 A | 1/1965 | Disston |
| 3,315,802 A | 4/1967 | Maro |
| 3,329,261 A | 7/1967 | Serany, Jr. et al. |
| 3,379,339 A | 4/1968 | Asenbauer |
| 3,485,352 A | 12/1969 | Pilger |
| D218,077 S | 7/1970 | Gabriel |
| 3,542,019 A | 12/1970 | Gittins |
| 3,726,281 A | 4/1973 | Norton |
| 3,851,649 A | 12/1974 | Villari |
| D234,404 S | 2/1975 | Merril |
| D237,315 S | 10/1975 | Nowkowski |
| D237,317 S | 10/1975 | Norkowski |
| 3,967,728 A | 7/1976 | Gordon et al. |
| 3,976,195 A | 8/1976 | Cohen |
| 3,978,983 A | 9/1976 | Brezetta |
| D242,654 S | 12/1976 | Rawls |
| 3,998,221 A | 12/1976 | Collins |
| D243,798 S | 3/1977 | Swartz |
| 4,011,944 A | 3/1977 | Cooley |
| 4,053,280 A | 10/1977 | Salisbury |
| 4,075,782 A | 2/1978 | Neuschatz |
| D248,871 S | 8/1978 | Forsman et al. |
| D249,362 S | 9/1978 | Forsman et al. |
| 4,160,505 A | 7/1979 | Rauschenberger |
| 4,170,300 A | 10/1979 | Pick |
| 4,226,328 A * | 10/1980 | Beddow ............... A61F 17/00 206/364 |
| 4,266,669 A | 5/1981 | Watson |
| 4,282,678 A | 8/1981 | Tsui |
| 4,307,539 A | 12/1981 | Klein |
| D262,995 S | 2/1982 | Gaba et al. |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D280,993 S | 10/1985 | Mariol |
| D283,051 S | 3/1986 | Fichera |
| D287,760 S | 1/1987 | Discko, Jr. |
| 4,761,008 A | 8/1988 | Huggins |
| 4,767,008 A | 8/1988 | Warnecke et al. |
| 4,795,441 A * | 1/1989 | Bhatt ................. A61G 7/0503 128/DIG. 26 |
| 4,828,113 A | 5/1989 | Friedland |
| 4,844,259 A | 7/1989 | Glowczewskie, Jr. et al. |
| 4,858,821 A * | 8/1989 | Bickelhaupt ........ A61M 25/002 206/364 |
| D310,896 S | 9/1990 | Winjum |
| 4,991,877 A | 2/1991 | Lieberman |
| 5,007,535 A | 4/1991 | Meseke et al. |
| 5,024,326 A | 6/1991 | Sandel et al. |
| 5,031,768 A * | 7/1991 | Fischer ........................ 206/370 |
| 5,094,621 A | 3/1992 | Friedel |
| 5,163,557 A | 11/1992 | Sokolowski |
| 5,170,804 A | 12/1992 | Glassman |
| 5,197,885 A | 3/1993 | Friedel |
| D334,973 S | 4/1993 | Valentine et al. |
| D337,830 S | 7/1993 | Coyne et al. |
| 5,232,369 A | 8/1993 | Mavrikis |
| 5,244,394 A | 9/1993 | Serabian-Musto |
| D343,687 S | 1/1994 | Houghton et al. |
| 5,312,287 A | 5/1994 | Chuang |
| 5,314,339 A | 5/1994 | Aponte |
| 5,318,543 A | 6/1994 | Ross et al. |
| 5,324,201 A | 6/1994 | Friedel |
| 5,339,955 A * | 8/1994 | Horan et al. ................. 206/370 |
| D351,661 S | 10/1994 | Fischer |
| 5,392,918 A | 2/1995 | Harrison |
| 5,411,437 A | 5/1995 | Weber et al. |
| 5,487,566 A | 1/1996 | Hedge, Jr. |
| D380,272 S | 6/1997 | Partika et al. |
| 5,665,945 A | 9/1997 | Oshima |
| D387,177 S | 12/1997 | Davis |
| D387,559 S | 12/1997 | Williamson |
| 5,713,778 A | 2/1998 | Rodeosevich et al. |
| 5,720,502 A | 2/1998 | Cain |
| 5,778,574 A | 7/1998 | Reuben |
| 5,779,053 A | 7/1998 | Partika |
| 5,795,213 A | 8/1998 | Goodwin |
| 5,820,441 A | 10/1998 | Pracas |
| 5,827,262 A | 10/1998 | Neftel et al. |
| 5,829,790 A | 11/1998 | Phillips |
| 5,872,262 A | 2/1999 | Dolle, III et al. |
| 5,941,241 A | 8/1999 | Weinstein et al. |
| 5,947,284 A | 9/1999 | Foster |
| 5,954,369 A | 9/1999 | Seabrook |
| 5,975,295 A | 11/1999 | Diamond |
| 6,004,136 A | 12/1999 | Ehrenpreis |
| 6,012,586 A * | 1/2000 | Misra ................. A61B 50/30 206/370 |
| 6,068,121 A | 5/2000 | McGlinch |
| 6,089,943 A | 7/2000 | Lo |
| 6,142,152 A | 11/2000 | Gawarecki |
| 6,158,437 A | 12/2000 | Vagley |
| 6,159,017 A | 12/2000 | Coomansingh |
| D442,697 S | 5/2001 | Hajianpour |
| D450,130 S | 11/2001 | Goldstein |
| D450,391 S | 11/2001 | Hunt et al. |
| 6,330,427 B1 | 12/2001 | Tabachnik |
| 6,361,396 B1 | 3/2002 | Snyder et al. |
| 6,382,212 B1 | 5/2002 | Borchard |
| 6,405,863 B1 | 6/2002 | Dhindsa |
| 6,454,097 B1 | 9/2002 | Blanco |
| 6,579,271 B1 | 6/2003 | Aruffo et al. |
| 6,659,506 B1 | 12/2003 | Erisalu |
| 6,681,933 B1 | 1/2004 | Demsien et al. |
| 6,769,546 B2 | 8/2004 | Busch |
| D495,491 S | 9/2004 | Ramirez |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,915,901 B2 | 7/2005 | Feinberg |
| 6,926,708 B1 | 8/2005 | Franks-Farah et al. |
| 6,948,742 B2 | 9/2005 | Buck |

(56) References Cited

U.S. PATENT DOCUMENTS

| | | | |
|---|---|---|---|
| 7,048,120 | B2 | 5/2006 | Pond |
| 7,066,328 | B2 | 6/2006 | Pulsifer |
| D530,920 | S | 10/2006 | Snell |
| D547,064 | S | 7/2007 | Snell |
| D549,454 | S | 8/2007 | Ahman |
| 7,264,869 | B2 | 9/2007 | Tobita |
| 7,278,987 | B2 | 10/2007 | Solazzo |
| D557,047 | S | 12/2007 | Dretzka |
| D561,473 | S | 2/2008 | Phillips et al. |
| D563,673 | S | 3/2008 | Dretzka |
| 7,401,703 | B2 | 7/2008 | McMichael |
| 7,434,687 | B2 | 10/2008 | Itou et al. |
| D579,662 | S | 11/2008 | Dretzka |
| D590,596 | S | 4/2009 | Dretzka |
| D596,311 | S | 7/2009 | Antons |
| 7,624,869 | B2 | 12/2009 | Primer |
| D609,819 | S | 2/2010 | Tomes et al. |
| D612,153 | S | 3/2010 | Liao |
| 7,785,312 | B2 | 8/2010 | Thorne |
| D638,137 | S | 5/2011 | Gross et al. |
| D662,218 | S | 6/2012 | Pittman |
| 8,448,786 | B2 | 5/2013 | Tomes et al. |
| D688,461 | S | 8/2013 | Ambrefe et al. |
| 8,628,549 | B2 | 1/2014 | To et al. |
| 8,631,935 | B2 | 1/2014 | Tomes et al. |
| 8,678,190 | B2 | 3/2014 | Tomes et al. |
| 8,708,999 | B2 | 4/2014 | Hong |
| D708,347 | S | 7/2014 | Lober |
| D708,759 | S | 7/2014 | Heyman et al. |
| D720,470 | S | 12/2014 | Lober |
| D720,471 | S | 12/2014 | Angel et al. |
| 9,283,352 | B2 | 3/2016 | Tomes et al. |
| 9,522,753 | B2 | 12/2016 | Tomes et al. |
| 2002/0185406 | A1 | 12/2002 | Massengale |
| 2003/0031995 | A1 | 2/2003 | Laura |
| 2003/0038475 | A1 | 2/2003 | Stancil |
| 2003/0075474 | A1 | 4/2003 | Moyer et al. |
| 2003/0159969 | A1 | 8/2003 | McMichael et al. |
| 2004/0004019 | A1* | 1/2004 | Busch .................... 206/571 |
| 2004/0161732 | A1 | 8/2004 | Stump |
| 2004/0180822 | A1* | 9/2004 | Grafton .................. A61L 27/34 514/2.4 |
| 2004/0195145 | A1 | 10/2004 | Roshdy |
| 2004/0238391 | A1 | 12/2004 | Pond |
| 2005/0022822 | A1 | 2/2005 | Santilli |
| 2005/0101905 | A1 | 5/2005 | Merry |
| 2005/0228691 | A1 | 10/2005 | Paparo |
| 2005/0256453 | A1 | 11/2005 | Nagamatsu |
| 2005/0285385 | A1 | 12/2005 | Bova |
| 2006/0009742 | A1 | 1/2006 | Solazzo |
| 2006/0029912 | A1 | 2/2006 | Kearby et al. |
| 2006/0088355 | A1 | 4/2006 | Ribi |
| 2006/0186010 | A1 | 8/2006 | Warnack |
| 2006/0264822 | A1 | 11/2006 | Nagamatsu |
| 2006/0271019 | A1 | 11/2006 | Stoller |
| 2007/0026472 | A1 | 2/2007 | Prokash et al. |
| 2007/0060908 | A1 | 3/2007 | Webster et al. |
| 2007/0065792 | A1 | 3/2007 | Schubarth |
| 2007/0084742 | A1* | 4/2007 | Miller ................ A61B 17/3472 206/438 |
| 2007/0088330 | A1 | 4/2007 | House |
| 2007/0095699 | A1 | 5/2007 | Frieze |
| 2007/0142786 | A1 | 6/2007 | Lampropoulos |
| 2007/0161971 | A1 | 7/2007 | House |
| 2007/0225687 | A1 | 9/2007 | House |
| 2007/0299431 | A1 | 12/2007 | Jakubowski et al. |
| 2008/0116106 | A1 | 5/2008 | Lampropoulos et al. |
| 2008/0121553 | A1 | 5/2008 | Gobel |
| 2008/0221515 | A1 | 9/2008 | Nagamatsu |
| 2008/0283426 | A1 | 11/2008 | Primer et al. |
| 2008/0283433 | A1 | 11/2008 | Primer |
| 2009/0071854 | A1 | 3/2009 | Martin |
| 2009/0152160 | A1 | 6/2009 | Thompson et al. |
| 2009/0184026 | A1 | 7/2009 | Massengale et al. |
| 2009/0194453 | A1 | 8/2009 | Thorne et al. |
| 2009/0234346 | A1 | 9/2009 | McBride et al. |
| 2009/0236259 | A1 | 9/2009 | Hicks |
| 2010/0274205 | A1 | 10/2010 | Morelli et al. |
| 2010/0307942 | A1 | 12/2010 | Tomes et al. |
| 2010/0311026 | A1 | 12/2010 | Tomes et al. |
| 2011/0107494 | A1 | 5/2011 | Haines |
| 2011/0155599 | A1 | 6/2011 | Yakel et al. |
| 2011/0297147 | A1 | 12/2011 | Lick et al. |

FOREIGN PATENT DOCUMENTS

| | | |
|---|---|---|
| WO | WO-2005/027767 | 3/2005 |
| WO | WO-2006/114466 | 11/2006 |
| WO | WO-2007/045943 | 4/2007 |

OTHER PUBLICATIONS

"IPR 2015-00514—Patent Owner's Objection to Evidence", IPR 2015-00514—Patent Owner's Objection to Evidence Submitted During a Preliminary Proceeding; U.S. Pat. No. 8,678,190; Mailed Jul. 13, 2015.

"IPR 2015-00514—Patent Owner's Request for Adverse Judgement", U.S. Pat. No. 8,678,190; Mailed Jun. 23, 2015.

"IPR2015-00514—Scheduling Order", U.S. Pat. No. 8,678,190; Mailed Jun. 26, 2015.

"IPR2015-00514 Judgement—Termination of Proceeding", U.S. Pat. No. 8,678,190; Mailed Jul. 24, 2015.

"Australian First Exam Report", AU Patent Application No. 2011351971; Patent Examination Report No. 1; dated Jul. 25, 2015.

Poon, Robert "Final OA", U.S. Appl. No. 14/265,920, filed Apr. 30, 2014; dated Oct. 2, 2015.

Hand, Melanie J., "NonFinal OA", U.S. Appl. No. 14/165,044, filed Jan. 27, 2014; dated Oct. 26, 2015.

Poon, Robert "NonFinal OA", U.S. Appl. No. 14/718,792, filed May 21, 2015; dated Nov. 19, 2015.

Vasat, Peter "Notice of Allowance", U.S. Appl. No. 12/785,064, filed May 21, 2010, dated Sep. 12, 2016.

*Medline Industries* vs. *CR Bard, Inc*; No. 14-cv-3618; C.R. Bard's LPR 3.1 Contentions; Filed Nov. 24, 2015.

"Office Action Received", Chinese App No. 201280035246.1: NonFinal OA; dated Sep. 16, 2015.

"Office Action", Australian Application No. 2011351971; Reference No. 35204298/GP; dated Feb. 18, 2016.

Notice of Allowance; EP Application No. 10251025.2-1501; Reference P112645EP00; dated Feb. 18, 2016.

Mackenzie, Kristian "Office Action", Canadian Application No. 2,705,670; Ref No. 15468-8; dated Apr. 25, 2016.

Hand, Melanie Jo "Appeal Decision", U.S. Appl. No. 12/785,064, filed May 21, 2010; Mailed May 18, 2016.

Poon, Robert "NonFinal OA", U.S. Appl. No. 15/067,903; filed Mar. 11, 2016, dated Jun. 30, 2016.

"Notice of Acceptance", Australian Application No. 2011351971; Filed Dec. 30, 2011; dated May 13, 2016.

"Office Action", Chinese Application No. 201280035246.1; Filed May 11, 2012; dated Jul. 15, 2016.

*Medline Industries Inc.* vs *C.R. Bard, Inc*; C.R. Bard's LPR 3.1 Contentions; Civil Action No. 1:16-cs-3529; Judge Sharon Johnson Coleman; Filed Aug. 26, 2016.

"Medline Catalog", *Turkel Safety Thoracentesis Procedure Trays by Covidien*; http://www.medline.com/jump/sku/x/MDPKDL566059; Unknown Publication date but believed to be prior to present application filing date.

"Medline Catalog", *Turkel Safety Thoracentesis Procedure Trays by Covidien*; 5"; http://www.medline.com/sku/item/MDPKDL566075; Unknown Publication date but believed to be prior to present application filing date.

"Medline Catalog", Paracentesis Trays by Covidien; http://www.medline.com/sku/item/MDPSWD568006; Unknown Publication Date but believed to be prior to filing of present application.

"Medline Catalog", *Argyle Turkel Safety Thoracentesis System by Covidien*; http://www.medline.com/sku/item/MDPKDL5014; Unknown Publication Date but believe to be prior to filing of present application.

(56) References Cited

OTHER PUBLICATIONS

"Medline Catalog", *Argyle Trocar Catheter Kits by Covidien*; http://www.medline.com/sku/item/MDPSWD565028; Unknown Publication Date but believed to be prior to filing of present application.
"Medline Catalog", *Paracentesis Trays by Halyard Health*; http://www.medline.com/sku/item/MDPBAA61450. Unknown Publication Date but believed to be prior to filing of present application.
"Medline Catalog", *Safe-T Thoracentesis/Paracentesis Tray by Carefusion*; http://www.medline.com/sku/item/MDPBXTTPT1000SP; Unknown publication date but believed to be prior to filing of present application.
"Medline Catalog", *Thoracentesis Trays by Carefusion*; http://www.medline.com/sku/item/MDPBXTPIG1280K; Unknown publication date but believed to be prior to filing of present application.
"Medline Catalog", *Argyle Turkel Safety Thoracentesis System by Covidien*; 6"; http://www.medline.com/sku/item/MDPKDL5016; Unknown Publication Date but believed to be prior to filing of present application.
Marcetich, Adam "Notice of Allowance", U.S. Appl. No. 13/860,902, filed Apr. 11, 2013, dated Sep. 14, 2016.
Cavanna, Mark "Non-Final Office Action", U.S. Appl. No. 29/479,600, filed Jan. 17, 2014; dated Sep. 26, 2016.
Poon, Robert "Final OA", U.S. Appl. No. 15/067,903, filed Mar. 11, 2016; dated Jan. 13, 2017.
Marcetich, Adam "Notice of Allowance", U.S. Appl. No. 14/165,044, filed Jan. 27, 2014, dated Feb. 28, 2017.
Mackenzie, Kristian "Office Action", Canadian Application No. 2,705,670, dated Feb. 10, 2017.
Mackenzie, Kristian "Office Action", Canadian Application No. 2,705,647; dated Feb. 10, 2017.
Hand, Melanie J., "Notice of Allowance", U.S. Appl. No. 13/860,902, filed Apr. 11, 2013; dated Aug. 4, 2015.
"Office Action", Chinese Application No. 201280035246.1; Filed May 11, 2012; Reference No. 10055U CIP5 CN; dated Nov. 28, 2016.
Hand, Melanie J., "NonFinal OA", U.S. Appl. No. 13/860,902, filed Apr. 11, 2013, dated Apr. 1, 2016.
Poon, Robert "Appeal Decision", U.S. Appl. No. 13/153,300, filed Jun. 3, 2011; dated Oct. 12, 2016.
Long, Fonya M "Appeal Decision", U.S. Appl. No. 13/154,265, filed Jun. 3, 2011; dated Oct. 6, 2016.
Poon, Robert "Appeal Decision", U.S. Appl. No. 13/374,509, filed Dec. 30, 2011; Mailed Oct. 24, 2016.
"Second Office Action", Chinese Application No. 201280035240.4; dated Jun. 23, 2016.
Mackenzie, Kristian "Office Action", Canadian Application No. 2,705,647; Ref No. 15468-P37235CA00; dated Apr. 21, 2016.
Chinese Application No. 201280035240.4; Filed May 24, 2012; dated Aug. 18, 2015.
Hand, Melanie Jo "Final OA", U.S. Appl. No. 13/860,902, filed Apr. 11, 2013; dated May 22, 2015.
Schultz, Ottmar "Extended European Search Report", EP Application No. 16177903.8-1501; Filed Jun. 30, 2009; dated Oct. 27, 2016.
Marcetich, Adam "Notice of Allowance", U.S. Appl. No. 13/860,902, filed Apr. 11, 2013; dated Nov. 8, 2016.
Marcetich, Adam M., "Final OA", U.S. Appl. No. 14/165,044, filed Jan. 27, 2014, dated Aug. 11, 2016.
"Intent to Grant", Chinese Application No. 201180066491.4: Flled Dec. 30, 2011; dated Jul. 6, 2016.
Poon, Robert "Notice of Allowance", U.S. Appl. No. 14/718,792, filed May 21, 2015; dated Feb. 2, 2016.
"Office Action", Chinese Application No. 201180066491.4; dated Nov. 11, 2015.
"IPR2015-00513—Patent Owner's Request for Adverse Judgement", U.S. Pat. No. 8,631,935, dated Jul. 23, 2015.
Poon, Robert "Final Office Action", U.S. Appl. No. 14/718,792, filed May 21, 2015; dated Jan. 5, 2016.

*Medline Industries, Inc.* vs *C.R. Bard, Inc*; No. 1:14-cv-03618; Medline Industries Inc's Opposition to C.R.Bard Inc's Motion for Leave to File Second Amended Answer to Add Counterclaim; Filed Oct. 20, 2015.
*Medline Industries, Inc.* vs *C.R. Bard. Inc*; No. 1:14-cv-03618; Notice of Medline Industries Inc's Motion to Dismiss C.R. Bard Inc's Inequitable Conduct Counterclaim and to strike affirmative defense for the '786 Patent; Filed Oct. 20, 2015.
"IPR2015-00513—Request for Adverse Judgement", IPR2015-00513—Request for Adverse Judgement; Granted—Proceedings Terminated; U.S. Pat. No. 8,631,935; Entered Aug. 11, 2015.
"IPR0215-00513 Scheduling Order", U.S. Pat. No. 8,631,935; Mailed Jul. 15, 2015.
Cavanna, Mark "Final OA", U.S. Appl. No. 29/479,600, filed Jan. 17, 2014; dated Jun. 1, 2017.
Marcetich, Adam "Notice of Allowance"; U.S. Appl. No. 14/793,455, filed Jul. 7, 2015; dated Jul. 20, 2017.
*Medline Industries, Inc.* vs *C.R. Bard, Inc*; No. 1:14-cv-03618; Defendant C.R. Bards, Inc's Second Amended Answer to Second Amended Complaint; Filed Sep. 25, 2015.
*Medline Industries, Inc.* vs *C.R. Bard, Inc*; No. 14-cv-3618; Memorandum in Support of C.R. Bard's Motion for Leave to File Second Amended Answer to Add Counterclaim. Filed Sep. 25, 2015.
"IPR2015-00514 Decision Institution of Inter Partes Review", IPR2015-00514; U.S. Pat. No. 8,678,190, mailed Jun. 26, 2015; Decision Institution of Inter Partes Review.
"IPR2015-00509 Institution Decision", IPR2015-00509; U.S. Pat. No. 8,448,786; Mailed Jul. 15, 2015; Decision Denying Institution of Inter Partes.
"IPR 2015-00514 Petitioner's Request for Rehearing", IPR 2015-00514 Petitioner's Request for Rehearing; U.S. Pat. No. 8,678,190; Dated Jul. 10, 2015.
"IPR2015-00511 Institution Decision", IPR2015-00511; U.S. Pat. No. 8,631,935; Entered Jul. 15, 2015; Decision Denying Institution of Inter Partes Review.
"IPR2015-00513 Institution Decision", IPR2015-00513 Institution Decision; U.S. Pat. No. 8,631,935; Entered Jul. 15, 2015; Decision Institution of Inter Partes Review.
Marcetich, Adam. Non-Final Office Action, U.S. Appl. No. 14/793,455, filed Jul. 7, 2015; dated May 3, 2017.
Office Action, Chinese Application No. 201280035240.4; dated Apr. 1, 2017.
Poon, Robert. Final Office Action, U.S. Appl. No. 14/718,792, filed May 21, 2015; dated Jan. 5, 2016.
Poon, Robert. Notice of Allowance, U.S. Appl. No. 15/067,903; dated Aug. 23, 2017.
Pothier, Andrew. Office Action, Canadian Application No. 2,822,905; Reference No. 15468-P44352CA00; dated May 1, 2017.
"DVD", Entitled "*Preventing UTI: Care and Catheterization Techniques*"; Publication Date unknown but believed to be prior to 2007.
Poon, Robert "Non-Final Office Action", U.S. Appl. No. 12/495,148, filed Jun. 30, 2009; first inventor: Jennifer E. Tomes; dated Aug. 4, 2010.
Yuan, Minqiang "Non-Final Office Action", Chinese Application No. 200920267201.2, dated Sep. 9, 2010.
European Patent Office, "Extended EPO Search Report", EPO Application No. 10251025.2, In the Name of Medline Industries, dated Sep. 29, 2010.
Medline, "Medline Aritcle/Brochure", Published 2008.
Yuan, Minquiang "Non-Final Office Action", Chinese Application No. 200920267201.2; dated Jun. 4, 2010.
European Patent Office, "Extended EPO Search Report", Application No. 10251024.5, In the Name of Medline Industries, dated Oct. 18, 2010.
Chinese Patent Office "First Office Action", CN Application No. 201020219785.9; dated Nov. 18, 2010; Filed Jun. 3, 2010.
Poon, Robert "Final Office Action", U.S. Appl. No. 12/495,148, flled Jun. 30, 2009, dated Mar. 3, 2011.
Prange, Sharon M., "Response to First Office Action", U.S. Appl. No. 12/004,796, filed Dec. 21, 2007; dated Oct. 28, 2009.
Cavanna, Mark "Notice of Allowance", U.S. Appl. No. 29/362,279, filed May 21, 2010, dated Sep. 19, 2011.

(56) References Cited

OTHER PUBLICATIONS

Poon, Robert "NonFinal Office Action", U.S. Appl. No. 12/846,675, filed Jul. 29, 2010; dated Dec. 22, 2011.
Cavanna, Mark "Notice of Allowance", U.S. Appl. No. 29/338,022, filed Jun. 3, 2009; dated Oct. 1, 2009.
Cavanna, Mark "NonFinal Office Action", U.S. Appl. No. 29/380,474, filed Dec. 26, 2012; dated Mar. 27, 2012.
Poon, Robert "NonFinal Office Action", U.S. Appl. No. 12/647,515, filed Dec. 27, 2009; dated Jun. 28, 2012.
Cavanna, Mark "Ex Parte Quayle Action", U.S. Appl. No. 29/380,474, filed Dec. 6, 2010; Mailed Aug. 14, 2012.
Poon, Robert "Restriction Requirement", U.S. Appl. No. 12/647,515, filed Dec. 27, 2009; dated May 23, 2012.
Byun, Sung C., "PCT Search Report", PCT/US2011/068193; Filed Dec. 30, 2011; dated Aug. 22, 2012.
Poon, Robert "Final Office Action", U.S. Appl. No. 12/846,675, filed Jul. 29, 2010; dated Sep. 26, 2012.
Poon, Robert "NonFinal Office Action", U.S. Appl. No. 13/374,509, filed Dec. 30, 2011; dated Oct. 2, 2012.
Poon, Robert "NonFinal Office Action", U.S. Appl. No. 13/153,300, filed Jun. 3, 2011; dated Oct. 1, 2012.
Poon, Robert "NonFinal OA", U.S. Appl. No. 12/495,148, filed Jun. 30, 2009; dated Oct. 4, 2012.
Byun, Sung C., "PCT Search Report", PCT/US2012/039311; Filed May 24, 2011; dated Oct. 25, 2012.
Hand, Melanie J., "NonFinal OA", U.S. Appl. No. 13/155,026, filed Jun. 7, 2011; dated Nov. 30, 2012.
Byun, Sung Cheal "PCT Search Report and Written Opinion", PCT/US2012/037524; Filed May 11, 2012; dated Nov. 16, 2012.
"EPO Intent to Grant", EPO Application No. 10251024.5; Filed Jun. 2, 2010; dated Nov. 2, 2012.
Hand, Melanie J., "NonFinal OA", U.S. Appl. No. 12/785,064, filed May 21, 2010; dated Feb. 1, 2013.
Pass, Natalie "NonFinal OA", U.S. Appl. No. 13/153,265, filed Jun. 3, 2011; dated Mar. 5, 2013.
Hand, Melanie J., "Notice of Allowance", U.S. Appl. No. 13/155,026, filed Jun. 7, 2011; dated Feb. 1, 2013.
Hand, Melanie J., "NonFinal OA", U.S. Appl. No. 13/115,053, filed Jun. 7, 2011; dated May 9, 2013.
Poon, Robert "Final OA", U.S. Appl. No. 12/647,515, filed Dec. 27, 2009; dated May 13, 2013.
Hand, Melanie J., "Final OA", U.S. Appl. No. 12/785,064, filed May 21, 2010; dated Jun. 5, 2013.
Pass, Natalie "Final OA", U.S. Appl. No. 13/153,265, filed Jun. 3, 2011; dated Jul. 12, 2013.
Poon, Robert "Final Office Action", U.S. Appl. No. 12/495,148, filed Jun. 30, 2009; dated Jul. 31, 2013.
Poon, Robert "Final OA", U.S. Appl. No. 13/374,509, filed Dec. 30, 2011; dated Aug. 6, 2013.
Poon, Robert "Final OA", U.S. Appl. No. 13/153,300, filed Jun. 3, 2011; dated Aug. 6, 2013.
Poon, Robert "NonFinal OA", U.S. Appl. No. 12/846,675, filed Jul. 29, 2010; dated Sep. 10, 2013.
Cavanna, Mark "Notice of Allowance", U.S. Appl. No. 29/444,526, filed Jan. 31, 2013; dated Oct. 17, 2013.
Hand, Melanie J., "Notice of Allowance", U.S. Appl. No. 13/155,054, filed Jun. 7, 2011; dated Oct. 28, 2013.
Poon, Robert "Notice of Allowance", U.S. Appl. No. 12/495,148, filed Jun. 30, 2009; dated Nov. 20, 2013.
"Instructions", Naming a character website. URL: <https://web.archive.org/web/20080410122058/http://www.wilihow.com/Make-Your-Own-Anime-or-Mange-Character>. 2008.Retreived from Internet Dec. 10, 2013.
Naming Characters on Cards website. URL:<https://web.archive.org/web/20060219171403/http://www.hubbardscupboard.org/brown_bear_brown_bear.html>. (2006) . . . Retrieved form Internet Dec. 11, 2013.
Dictionary definition m-w. URL:<http://www.merriam-webster.com/dictionary/brave>. Retrieved fro Internet Dec. 10, 2013.

Dictionary definition m-w. URL:<http://ww.merriam-webster.com/dictionary/reassure>. Retrieved from Internet Dec. 10, 2013.
Lion King Sticker website. URL: <http://tlkobession.wuffpaws.org/OldSite/games/games2.html>. 1996 Retrieved from Internet Dec. 10, 2013.
Lion Sticker Activity Book website. URL: <http://www.amazon.com/Disneys-Simbas-Pride-Sticker-Activity/dp/B0018DOJZA>. 1998 Retrieved from Internet. Dec. 10, 2013.
"Examiner's Answer", U.S. Appl. No. 13/153,265, filed Jun. 3, 2011; dated Dec. 17, 2013.
Poon, Robert "NonFinal OA", U.S. Appl. No. 12/647,515, filed Dec. 27, 2009; dated Dec. 18, 2013.
Poon, Robert "Final OA", U.S. Appl. No. 12/846,675, filed Jul. 29, 2010; dated Dec. 18, 2013.
"Extended EPO Exam Report", EPO App No. 10251025.2; Filed Jun. 2, 2010; dated Dec. 17, 2013.
Poon, Robert "Notice of Allowance", U.S. Appl. No. 12/846,675, filed Jul. 29, 2010; dated Apr. 30, 2014.
Gimenez Burgos, R "Extended European Search Report", 11854003.8; Filed Dec. 30, 2011; dated Jun. 3, 2014.
"Bardex I.C. Infection Control Foley Tray", *Bard Infection Control System; Bardex I.C. Directions for Use Infection Control Foley Tray*; Copyright Dated 2006.
"Bardex I.C. Complete Care StateLock Device 350 ml Urine Meter Foley Tray with Bacteriostatic Collection System", *Bard Infection Control System; Bardex I.C. Complete Care Directions for Use*; Copyright Dated Sep. 2006.
"Bardex I.C. Infection Control 350ml Urine Meter Foley Tray", *Bard Infection Control System; Bardex I.C. Urine Meter Foley Tray Directions for Use*; Copyright Dated 2006.
"Bard Medical Division Care & Catheterization Script", *Care & Catheterization/Preventing UTI Script for education video; Preventing UTI: Care and Catheterization Techniques*; Copyright 2006; AV0512-06 R12/05 XXX.
*Medline Industries, Inc.* vs *C.R. Bard, Inc*; No. 14-cv-3618; C.R. Bard's LPR 2.3 Contentions—Initial Non-Infringement; Exhibits 1 and A-H; Dated Sep. 5, 2014.
*Medline Industries, Inc.* vs *C.R. Bard, Inc*; No. 1:14-cv-03618; Medline Industries, Inc.'s Response to C.R. Bard's Initial Invalidity Contentions; Exhibits A-H; Dated Sep. 19, 2014.
*Medline Industries, Inc.* vs *C.R. Bard, Inc*; No. 1:14-cv-03618; Responses to Medline Industries, Inc.'s First set of Requests for the Production of Documents; Dated Sep. 26, 2014.
*Medline Industries, Inc.* vs *C.R. Bard, Inc*; No. 1:14-cv-03618; Response to Medline Industries, Inc.'s First Set of Interrogatories; dated Sep. 26, 2014.
"Publication", European Commission: Pharmaceutical Committee "A Guideline on the Readability of the Label and Package Leaflet of Medicinal Products for Human Use"; Dated Sep. 29, 1998.
"Bard Publication", "*A few important words about Catheter Care*"; *C.R. Bard, Inc*; Copyright 2001 C.R. Bard, Inc.
Dover Intermittent Catheter Tray—14 fr, Red Rubber; Website http://tinyurl.com/o4esrwh; Unknown Publication Date.
"YouTube Training Video", https://www.youtube.com/watch?v=ISBya_5cIM.
"YouTube Training Video", https://www.youtube.com/watch?v=YwqcRUP35nl&list=UUG7a6tFPh1wvF0QDM Z3DarQ.
"NonFinal Office Action", U.S. Appl. No. 13/680,902, filed Apr. 11, 2014; dated Dec. 2, 2014.
"Inter Partes Review Petition for 8,448,786", U.S. Pat. No. 8,448,786; Filed Dec. 30, 2014; Mailed Dec. 30, 2014.
"Inter Partes Review Petition", IPR Exhibit—Kimmel Declaration U.S. Pat. No. 8,448,786; Dr. Robert M. Kimmel Declaration; Received Dec. 30, 2014.
"Inter Partes Review Petition", Exhibit; Kimmel CV—Dr. Robert M. Kimmel; Mailed Dec. 30, 2014.
"Inter Partes Review Petition", IPR Exhibit—Susan Carrow Declaration 8,448,786 patent; dated Dec. 30, 2014.
"Inter Partes Review Petition", Exhibit; Carrow CV—Susan Carrow CV; Mailed Dec. 30, 2014.
"Inter Partes Review Petition", Exhibit; EC Guideline 2009; "Guideline on the Readability of the Labelling and Package Leaflet

(56) References Cited

OTHER PUBLICATIONS of Medicinal Products for Human Use"; Revision 1 Published Jan. 12, 2009 (Dec. 1, 2009); Mailed Dec. 30, 2014.

"Inter Partes Review Petition", Exhibit—EC Guideline 1998; "*A Guideline on the Readability of the Label and Package Leaflet of Medicinal Products for Human Use*"; Published Sep. 29, 1998 (Sep. 29, 1998); Mailed Dec. 30, 2014.

"Inter Partes Review Petition", Exhibit—Soroka Glossary wrap; Illustrated Glossary of Packaging Terminology; second edition; publication date unknown.

"Inter Partes Review Petition", Exhibit—Soroka Glossary 'Bag'; *Illustrated Glossary of Packaging Terminology, second edition*; Walter Soroka; publication unknown.

"Inter Partes Review Petition", Exhibit—*Encyclopedia Dictionary of Medicine, Nursing and Allied Health*; Miller Keane, Seventh Edition.

"Inter Partes Review Petition", Exhibit—Dorland's Definition of Bag; *Dorland's Illustrated Medical Dictionary; 31st Edition*; Publication Date Unknown.

"Inter Partes Review Petition", Exhibit—Nursing Standard; Article in Learning Zone—Continue Professional Development; "*Reducing the risks associated with urinary catheters*"; Published Mar. 25, 2009.

"Inter Partes Review Petition", Exhibit—Websters Dictionary Definition of Dispose; *Webster's Third New International Dictionary*; Copyright 2003; publication date unknown.

"Inter Partes Review Petition", Exhibit—Bard DFU; *Bardex Infection Control Foley Tray*; Copyright 2006, publication date unknown.

"Inter Partes Review Petition", Exhibit—Medline Initial Infringement Contentions; *Medline Industries* vs. *C.R. Bard*; Dated Aug. 22, 2014.

"Inter Partes Review Petition", Exhibit—FDA Article; *Guidance for the Content of Premarkt Notifications fro Conventional and Antimicrobial Foley Catheters*; http://www.fda.gov/medicaldevices/deviceregulationandguidance/guidancedocuments/ucm080884.htm; Unknown Publication Date.

"Inter Partes Review Petition", Exhibit—Bardex DFU; *Directions for Use/Patient Education Information—Urology*; Unknown Publication Date.

"Inter Partes Review Petition", Exhibit—Mosby's Pocket Guide Excerpt; *Mosby's Pocket Guide to Basic Skills and Procedures*; Sixth Edition; Perry & Potter; "Urinary Catheter: Indwelling, Straight, Care and Removal"; Unknown Publication Date.

"Inter Partes Review Petition", Exhibit—Health Protection Scotland; CAUTI Maintenance Bundel; Version 2, Feb. 2008.

"Inter Partes Review Petition", Exhibit—FAQs "Catheter-Associated Urinary Tract Infection"; Unknown Publisher; Unknown Publication Date.

"Inter Partes Review Petition for U.S. Pat. No. 8,631,935", Inter Partes Review Petition for U.S. Pat. No. 8,631,935 for claims 1-4 and 11-20; Filed Dec. 30, 2014.

"Inter Partes Review Petition for U.S. Pat. No. 8,631,935", Inter Partes Review Petition for U.S. Pat. No. 8,631,935 for Claims 7-8, 10, 21-23, 25, 27-28, and 30-34; Filed Dec. 30, 2014.

"Inter Partes Review Petition for U.S. Pat. No. 8,678,190", Inter Partes Review Petition for U.S. Pat. No. 8,678,190; Filed Dec. 30, 2014.

"Inter Partes Review Petition", Exhibit—Kimmel Declaration for U.S. Pat. No. 8,631,935 claims 1-4 and 11-20; Declaration of Dr. Robert M. Kimmel; Mailed Dec. 30, 2014.

"Inter Partes Review Petition", Exhibit—Declaration of Susan Carrow for U.S. Pat. No. 8,631,935 claims 1-4 and 11-20; Mailed Dec. 30, 2014.

"Inter Partes Review Petition", Exhibit—Response to Office Action in U.S. Appl. No. 12/495,148; Application Filed Jun. 30, 2009; Response Filed Nov. 19, 2010.

"Inter Partes Review Petition", Exhibit—RCE Filed November May 31, 2011 for U.S. Appl. No. 12/495,148; Application Filed Jun. 30, 2009.

"Inter Partes Review Petition", Exhibit—Amendment filed on Apr. 3, 2013 for U.S. Appl. No. 12/495,148; Application Filed Jun. 30, 2009.

"Inter Partes Review Petition", Exhibit—Infection Control Today Article; *Medical Center Cuts Catheterizations by 21 Percent with Foley Catheter Management System*; Published 2010.

"Inter Partes Review Petition", Exhibit—Morning Start Article; "*Floyd Medical Center Reduces Catheter-Associated Urinary Tract Infections 83 Percent and Catheter Use by 23 Percent*"; Published Jan. 2011.

"Inter Partes Review Petition", Exhibit—Medical News Today Article; '*Getting To Zero:' Medlines' Erase Cauti Program Helps Hospitals Reduce Catheter Use by 20 Percent*; Article Date Apr. 13, 2011.

"Inter Partes Review Petition", Exhibit—The Journal of Healthcare Contracting, Oct. 2012; "*Catheter-associated urinary tract infections*".

"Inter Partes Review Petition", IPR Exhibit—Kimmel Declaration for U.S. Pat. No. 8,631,935 claims 1-4 and 11-20; Declaration of Dr. Robert M. Kimmel; Mailed Dec. 30, 2014.

"Inter Partes Review Petition", IPR Exhibit—Carrow Declaration for U.S. Pat. No. 8,631,935 claims 1-4 and 11-20; Susan Carrow Declaration; Mailed Dec. 30, 2014.

"Inter Partes Review Petition", IPR Exhibit—Kimmel Declaration for U.S. Pat. No. 8,631,935 claims 7-8, 10, 21-23, 25, 27-28, and 30-34; Declaration of Dr. Robert M. Kimmel; Mailed Dec. 30, 2014.

"Inter Partes Review Petition", IPR Exhibit—Kimmel Declaration for U.S. Pat. No. 8,768,190; Declaration of Dr. Robert M. Kimmel; Mailed Dec. 30, 2014.

"Inter Partes Review Petition", IPR Exhibit—Carrow Declaration for U.S. Pat. No. 8,768,190; Declaration of Susan Carrow; Mailed Dec. 30, 2014.

Poon, Robert "NonFinal OA", U.S. Appl. No. 14/265,920, filed Apr. 30, 2014; dated Dec. 30, 2014.

Gimenez Burgos, R "European Examination Report", European Application No. 11 854 003.8-1659; Ref SJG/P128064EP00; dated Jan. 22, 2015.

Gimenez Burgos, R "Extended European Search Report", EPO App No. 12 79 3939; Reference No. SJG/P130269EP00; dated Jan. 27, 2015.

Gimenez Burgos, R "Extended European Search Report", EU App No. 12792423.1-1659/2713933; PCT/US2012039311; REference No. SJG/P130270EP00; dated Jan. 27, 2015.

"Bard IPR Exhibit", "Inter Partes Review Petition", IPR Exhibit—Carrow Declaration for U.S. Pat. No. 8,631,935; Susan Carrow Declaration; Mailed Dec. 30, 2014.

"Article 94(3) EPC Examination", European Application No. 10 251 025.2-1501; Reference P112645EP00; dated Mar. 13, 2015.

Poon, Robert "Final OA", U.S. Appl. No. 12/647,515, filed Dec. 27, 2009; dated Apr. 7, 2015.

"Office Action", Chinese Application No. 201180066491.4; dated Mar. 24, 2015.

"Inter Partes Review—Patent Owner Response", Inter Partes Review—Patent Owner Response; U.S. Pat. No. 8,448,786; IPR2015-00509; Filed Apr. 22, 2015.

"Inter Partes Review—Patent Owner Response", Inter Partes Review—Patent Owner Response; U.S. Pat. No. 8,631,935; Inter Partes Review No. IPR2015-00511; Filed Apr. 22, 2015.

"Inter Partes Review—Patent Owner Response", Inter Partes Review—Patent Owner Response; U.S. Pat. No. 8,631,935; Inter Partes Review No. IPR2015-00513; Filed Apr. 21, 2015.

"Inter Partes Review—Patent Owner Response", Inter Partes Review—Patent Owner Response; U.S. Pat. No. 8,678,190; Inter Partes Review No. IPR2015-00514; Filed Apr. 21, 2015.

\* cited by examiner

CATHETER TRAY, PACKAGING SYSTEM, AND ASSOCIATED METHODS

CROSS REFERENCE TO PRIOR APPLICATIONS

This application is a continuation from, and claims priority and benefit under 35 USC §120 from, U.S. application Ser. No. 12/846,675, filed Jul. 29, 2010, now U.S. Pat. No. 8,746,452, which application is a divisional application from and claims priority and benefit under 35 USC §121 from, U.S. application Ser. No. 12/495,148, filed Jun. 30, 2009, now U.S. Pat. No. 8,631,935, which application claims priority and benefit under 35 USC §119(e) from Provisional Application No. 61/183,629, filed Jun. 3, 2009.

BACKGROUND

Technical Field

This invention relates generally to storage containers for medical devices, and more particularly to a storage container for a long, flexible medical implement, such as a catheter, and related medical devices.

Background Art

Medical devices, including surgical instruments, supplies, and so forth, are generally shipped from manufacturer to medical services provider in sterile packaging. For example, a scalpel may be shipped to a surgeon in a plastic, vacuum-sealed, sterile package. Similarly, bandages may be shipped in paper, plastic, or paper composite sterile wrappers. When the medical services provider is ready to use the medical supply, the sterile package is removed. The medical services provider then uses the object in accordance with the procedure being performed.

While conventional packaging works well for objects having a generally unchanging form factor, special considerations have to be taken into consideration for some medical supplies. By way of example, catheter assemblies and other flexible equipment is generally shipped in a coiled configuration. Once the sterile packaging is removed, the catheter must be uncoiled prior to use. Care must be taken in shipping, unwrapping, and using the catheter. For instance, if a catheter is inadvertently bent, kinked, or otherwise damaged, it may no longer be suitable for use. Compounding this issue, catheters are available in a variety of lengths ranging from 100 centimeters to over 250 centimeters.

Traditional catheters are packaged, for example, in individual packaging. The catheter and card are then sealed in a sterile plastic wrap. These catheters are prone to damage in shipment, storage, and when being unpacked, as the card and wrap provide little physical protection.

Some manufacturers have started shipping catheters and other similar devices in flat plastic trays. For example, U.S. Pat. No. 6,068,121 to McGlinch teaches one such tray. The tray has several specifically contoured loops such that one universal tray will accommodate several different sized catheters. Such packaging presents a problem, however, in that large amounts of storage space are taken with a universal tray, especially when a relatively short catheter is shipped therein. Additionally, when in use, these trays occupy large amounts of a medical service provider's sterile workspace or table, leaving little room for related components, such as lubricants, fluid bags, and so forth.

There is thus a need for an improved container for flexible medical devices or catheters that facilitates more effective and simpler deployment of the device during a procedure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
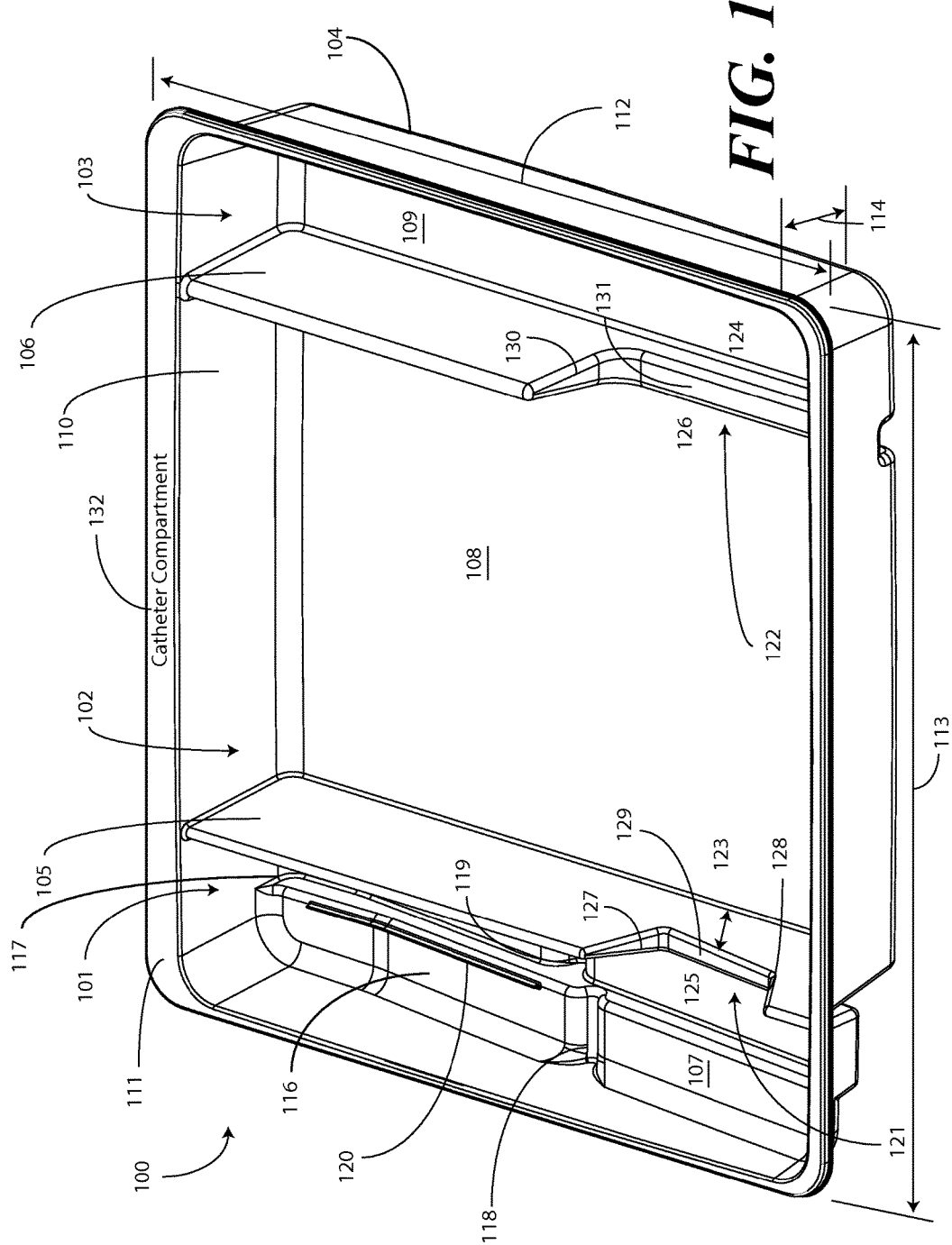
FIG. 1 illustrates a top, front, right perspective view of one embodiment of a tray for a catheter or similar assembly in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a tray configured to accommodate a coiled medical device such as a catheter or catheter assembly. In addition to accommodating the coiled medical device, embodiments of the present invention are also configured to contain devices and materials intended for use with the coiled medical device.

Using a catheter assembly as an example, when a catheter assembly is inserted into a patient, sterile water may be used to inflate the catheter. Additionally, the catheter may be coated in a lubricating jelly prior to insertion into the patient. Fluids and other samples may then be monitored and obtained from the patient via the catheter. Embodiments of the present invention provide a single container 100 configured to accommodate not only the catheter assembly 700 and fluid bag 730, but also syringes 701, 702 containing sterile water or lubricants. Further, the tray can accommodate a sterile specimen jar 703 or capturing samples taken from the patient via the catheter.

In addition to simply accommodating these corresponding medical devices, in one embodiment the tray is configured to provide the medical services provider with mnemonic devices instructing them in which order to use each device. For example, a compartment containing syringes, in one embodiment, includes an inclined, stair-stepped bottom member to present the plungers of each syringe at an easy to reach angle and at different heights based upon order of use.

Another advantage of embodiments of the present invention is that compartments have multi-purpose functionality. For example, in one embodiment, a container configured to accommodate a syringe having lubricating jelly disposed therein is also configured to be used as a lubricating jelly applicator. A medical services provider first dispenses the lubricating jelly into the syringe compartment. The medical services provider then passes the catheter from another compartment through an opening in a barrier separating the compartments into the lubricating jelly. As such, the tray not only serves as a shipping and storage container for an assembly of devices used with a catheter procedure, but also as an application device to assist a medical services provider in using those products together.

Figure 2:
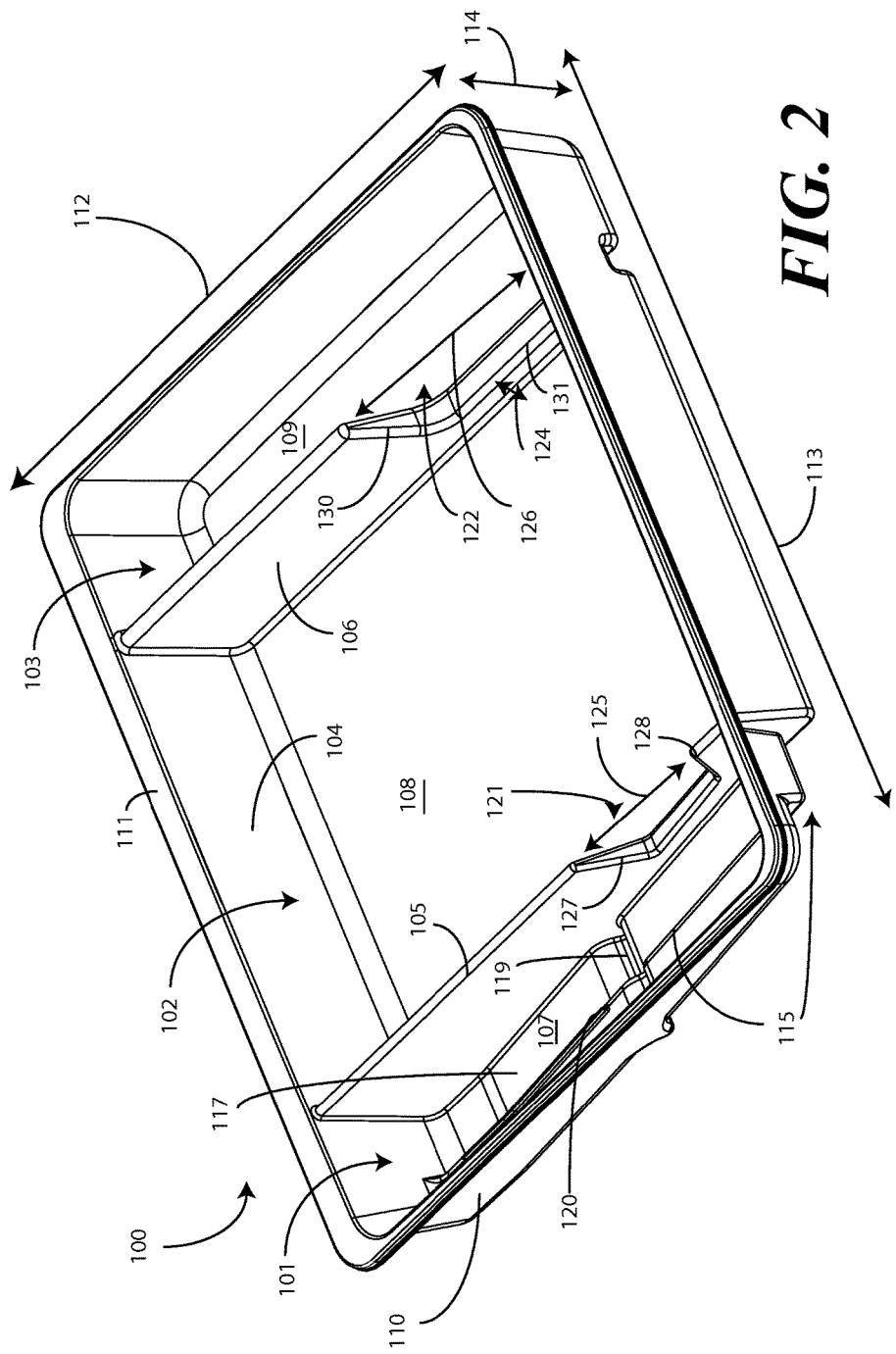
FIG. 2 illustrates a top, front, left perspective view of one embodiment of a tray for a catheter or similar assembly in accordance with embodiments of the invention.
Figure 3:
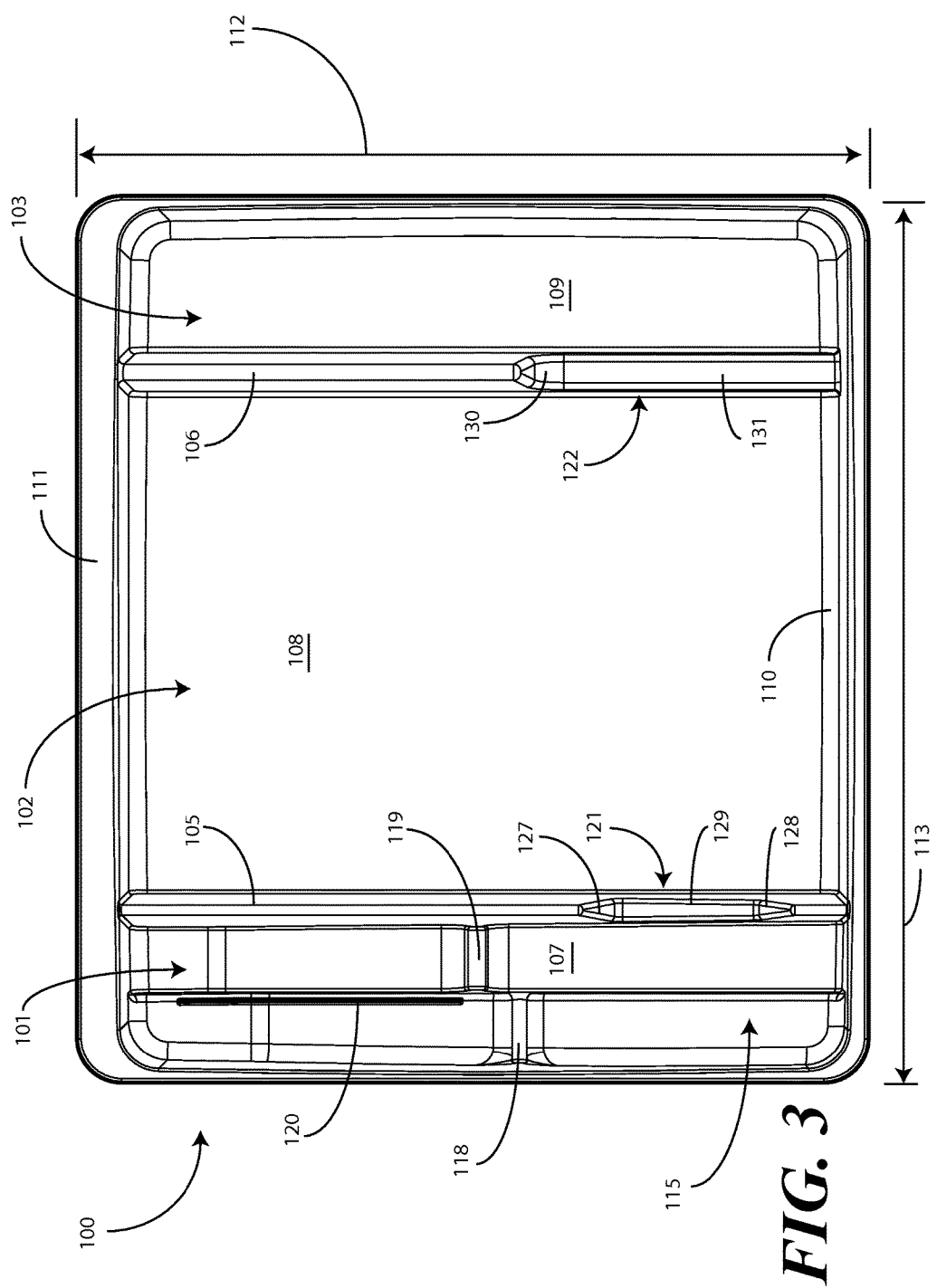
FIG. 3 illustrates a top plan view of one embodiment of a tray for a catheter or similar assembly in accordance with embodiments of the invention.
Figure 4:
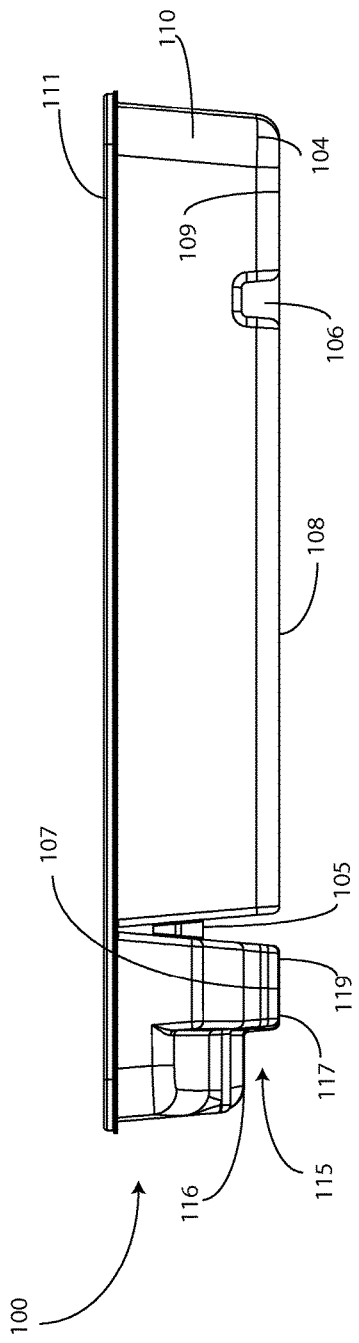
FIG. 4 illustrates a front elevation view of one embodiment of a tray for a catheter or similar assembly in accordance with embodiments of the invention.
Figure 5:
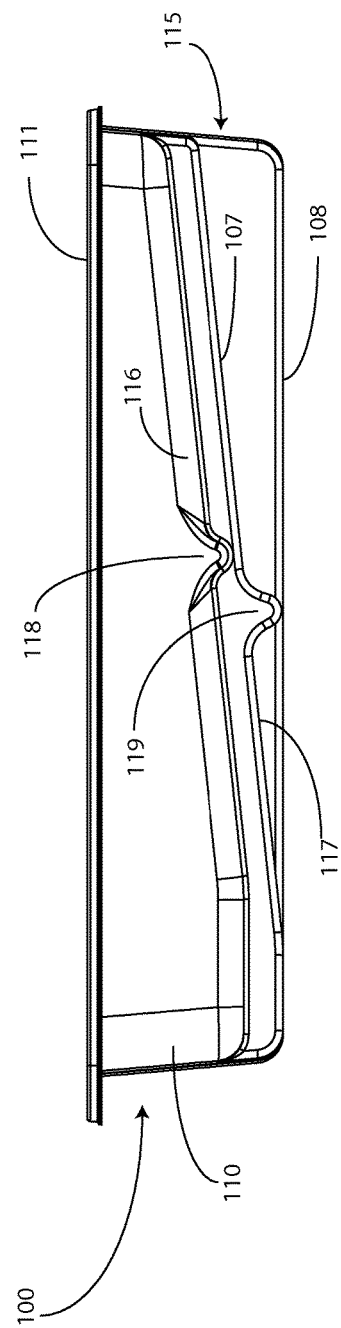
FIG. 5 illustrates a cut-away, left elevation view of one embodiment of a tray for a catheter or similar assembly in accordance with embodiments of the invention.
Figure 6:
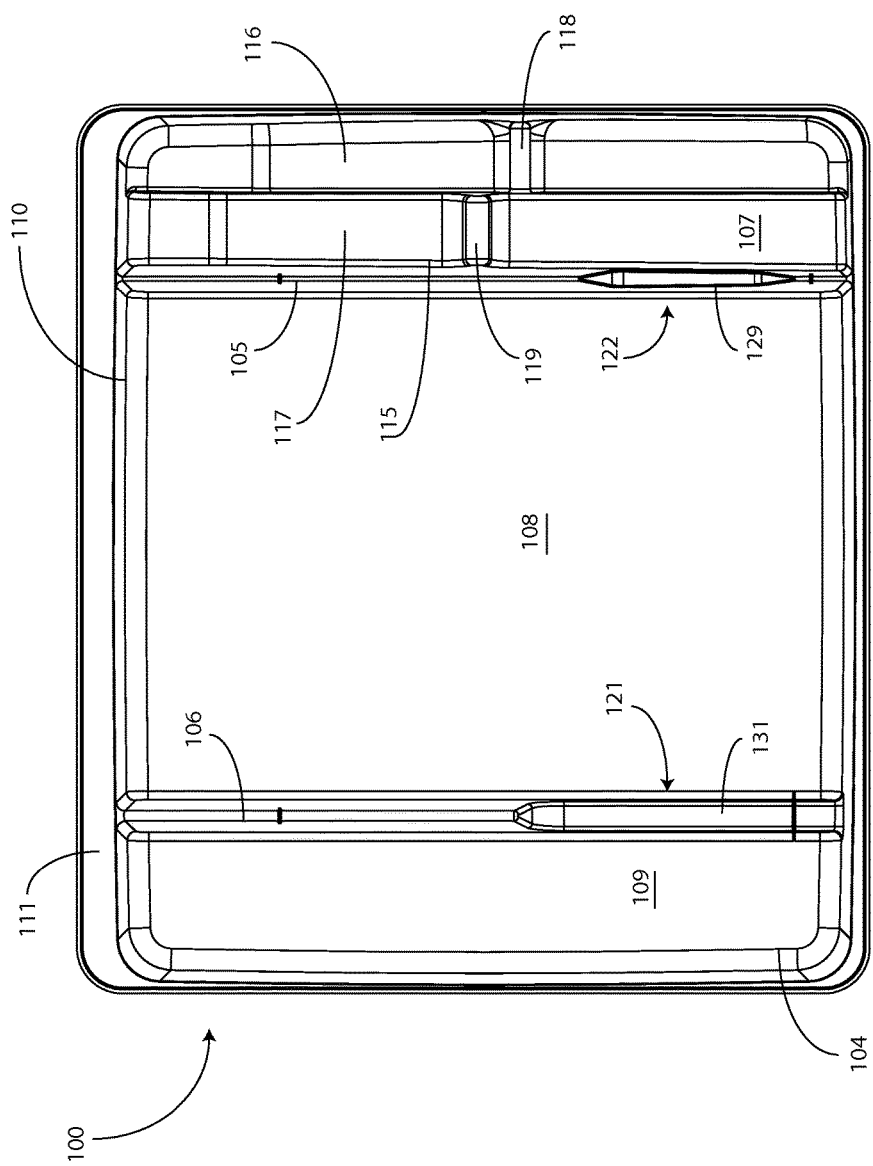
FIG. 6 illustrates a bottom plan view of one embodiment of a tray for a catheter or similar assembly in accordance with embodiments of the invention.

Turning now to FIGS. 1-6, illustrated therein are views of one embodiment of a tray 100 configured to accommodate a catheter assembly in accordance with embodiments of the invention. FIG. 1 illustrates a top, front right perspective view of the tray 100. FIG. 2 illustrates a top, front, left perspective view of the tray 100. FIG. 3 illustrates a top plan view of the tray 100. FIG. 4 illustrates a front elevation view of the tray 100. FIG. 5 illustrates a cut-away, left elevation view of one embodiment of a tray 100. Likewise, FIG. 6 illustrates a bottom plan view of the tray 100. For simplicity of discussion, these figures will be referred to collectively with like reference numerals referring to identical or functionally similar elements throughout the separate views.

The tray 100, in one embodiment, is formed by a contoured surface 104 that defines the various features and compartments of the tray 100. The contoured surface 104 of the tray 100 can be manufactured in various ways. For example, in one embodiment, the tray 100 can be thermally formed on a mold from a soft thermoplastic, such as styrene or polystyrene. In another embodiment, the tray 100 can be injection molded. In another embodiment, the tray can be poured on a mold using a quick setting plastic, epoxy, or resin. Other methods of manufacture will be obvious to those of ordinary skill in the art having the benefit of this disclosure.

Exemplary dimensions for one embodiment of the tray 100 are as follows: The length 112 can be between nine and twelve inches, such as ten inches. One illustrative length 112 may be 10.380 inches. Similarly, the width 113 can be between eight and eleven inches, such as nine inches. One illustrative width 113 is 9.250 inches. The height 114 can be between one and three inches. One illustrative height 114 is 1.750 inches.

In one embodiment, the tray 100 includes three main compartments: a first compartment 101, a second compartment 102, and a third compartment 103. The first compartment 101 is separated from the second compartment 102 by a first barrier 105. The second compartment 102 is separated from the third compartment 103 by a second barrier 106.

In one embodiment, the compartments are open from the top of the tray 100—the top being opposite the base members of the tray 100—and are bounded on the bottom by a first base member 107, a second base member 108, and a third base member 109. The compartments are bounded on the sides by a perimeter wall 110. In the illustrative "open top" embodiment of FIG. 1, the perimeter wall 110 ends in a horizontal flange 111 extending substantially orthogonally from the perimeter wall 110. It will be clear to those of ordinary skill in the art having the benefit of this disclosure that embodiments other than that shown in FIG. 1 are possible without departing from the spirit and scope of the invention. For instance, the top of the tray 100 could have a hinged or snap-coupled lid that is opened or removed to reveal the compartments there beneath.

In one illustrative embodiment, the tray 100 is configured to hold or otherwise accommodate all of the necessary devices and materials to perform a catheter-based procedure on a patient. Said differently, the tray 100 is configured to hold not only the catheter assembly, but the medical devices corresponding to catheter use as well. Using one illustrative procedure as an example, the following devices will be used: a syringe holding sterile water, a syringe holding lubricating jelly or another equivalent lubricant, a catheter assembly, skin cleansing or preparation materials, and a specimen jar. The various compartments and features of the tray 100 shown in FIGS. 1-6 will be described for use with these devices. As will be described in more detail below, additional objects can be included with the tray, such as one or more towels, a drape to cover the patient, rubber gloves, hand sanitizing materials, printed instructions, and so forth. The syringe holding sterile water, syringe holding lubricating jelly, catheter assembly, and specimen jar are used for illustration purposes only, as it will be clear that other objects may be added to or substituted for these objects. Further, subsets of these objects may be used.

In one embodiment suitable for procedures using the syringe holding sterile water, syringe holding lubricating jelly, catheter assembly, and specimen jar, in one embodiment, the tray 100 is configured such that these objects are ordered in accordance with their use during the procedure.

For example, in one embodiment the tray 100 includes a first compartment 101 for accommodating one or more syringes, a second compartment 102 for accommodating the catheter assembly, and a third compartment 103 for accommodating the specimen jar. These devices stowed in the various compartments will be illustrated and described with respect to FIGS. 7-10 below. The discussion of FIGS. 1-6 will include the features of the tray 100 that make the tray 100 suitable for accommodating these devices.

For example, in one embodiment the first compartment base member 107 includes a stair-stepped contour 115 suitable for accommodating a plurality of syringes at different heights. For example, a first step portion 116 of the stair-stepped contour 115 may be at a different height within the tray 100 than a second step portion 117 of the stair-stepped contour. In the illustrative embodiment of FIGS. 1-6, the first step portion 116—which is disposed farther from the first barrier 105 than the second step portion 117—is shallower than the second step portion 117. Said differently, the second step portion 117 is disposed at a greater depth within the tray 100 than the first step portion 116.

The stair-stepped contour 115 can be used as mnemonic device when multiple syringes are stored within the first compartment 101. For example, it may be intuitive that a syringe placed on a higher step portion may need to be used first. This intuition is further enforced when the higher step portion is disposed farther to the left in a left-to-right usage configuration. Thus, a user receives a mnemonic reminder to use a syringe disposed on the first step portion 116 prior to a syringe disposed on the second step portion 117, as it is both higher and farther to the left.

Where syringes are stowed in the first compartment 101, the first compartment base member 107 can further be configured for syringe ease of use. For example, in one embodiment the first compartment base member 107 is inclined relative to other compartment base members. In the illustrative embodiment of FIGS. 1-6, the second compartment base member 108 and third compartment base member 109 are substantially coplanar with each other. Further, the second compartment base member 108 and third compartment base member 109 are generally flat in these views, although it will be clear to those of ordinary skill in the art having the benefit of this disclosure that contours could be incorporated into one or both of these base members.

In this illustrative embodiment, however, the first compartment base member 107 is configured to be inclined relative to one or both of the second compartment base member 108 and third compartment base member 109. As such, the stair-stepped contour 115 forms a ramp upon which syringes may be placed so that the plunger of each syringe is predisposed to project upward and out of the tray 100. Said differently, the stair-stepped contour 115 is configured such that the first step portion 116 and the second step portion 117 are disposed in a non-parallel orientation relative to the second compartment base member 108. This configuration makes it easier for a medical services provider to grasp the syringes and remove them from the tray 100.

The first compartment base member 107 may include other features suitable for accommodating one or more syringes as well. In one embodiment, one or both of the first step portion 116 and second step portion 117 include recesses 118,119 for accommodating a syringe flange. These recesses 118,119 generally function to prevent the syringes from sliding lengthwise within the first compartment 101. Similarly, in one embodiment one or both of the first step portion 116 and the second step portion 117 include protrusions 120 that help to prevent the syringes from sliding laterally within the first compartment 101.

In one embodiment, one or both of the first barrier 105 and the second barrier 106 include openings disposed therein. In the illustrative embodiment shown in FIGS. 1-6, the first barrier 105 includes a first opening 121 between the first compartment 101 and the second compartment 102. Similarly, the second barrier 106 includes a second opening 122 between the second compartment 102 and the third compartment 103. Each of these openings has an opening depth associated therewith. Similarly, each opening has an opening width associated therewith. In the illustrative embodiment of FIGS. 1-6, the first opening 121 is bounded by a first opening base member 129 and two inclined first opening side members 127,128, while the second opening 122 is bounded by a second opening base member 131, an inclined second opening side member 130, and the perimeter wall 110.

While the opening depths can be the same, in one embodiment the opening depths are different. For example, in the illustrative embodiments of FIGS. 1-6, the first opening 121 has a first opening depth 123 that is less than the second opening depth 124 of the second opening 122. Similarly, in one embodiment the opening widths are different. For example, in the illustrative embodiments of FIGS. 1-6, the first opening 121 has a first opening width 125 that is less than the second opening width 126 of the second opening 122. Such a disparity in opening depths and widths, as well as the inclusion of inclined opening side members, provides an advantage in some applications.

For instance, in many catheter procedures a pair of syringes—such as syringes having a one-half inch diameter—fits easily into the first compartment 101 when the tray 100 is made with the illustrative dimensions set forth above. However, some procedures require one or more of the syringes to be larger. For example, some syringes are larger in diameter. These larger syringes are capable of nesting within the first opening 121 and second opening 122. The inclined opening side members prevent the syringe from moving lengthwise, while the disparate opening heights present the plunger of the syringe to the medical services provider for easy removal from the tray 100.

The stair-stepped contour 115, working in tandem with the first opening 121, gives the tray additional advantages over prior art catheter containers. For instance, when the first compartment 101 has a first compartment base member 107 configured with a stair-stepped contour 115, the first compartment 101 can be used as a lubricant applicator for the catheter.

Specifically, the medical services provider may dispense the lubricating jelly along the second step portion 117. As the second step portion 117 is lower in the tray 100 than the first step portion 116, the second step portion 117 serves as a channel in which the lubricating jelly may spread. A medical services provider may then pass the catheter through the first opening 121, through the channel formed by the second step portion 117, i.e., along the second step portion 117 through the dispensed lubricating jelly, and out the top of the tray 100 to the patient. This feature of the tray 100 greatly eases the application of lubricating jelly to the catheter when compared to prior art solutions. In one embodiment, the tray 100 is packaged with printed instructions showing the medical services provider how to apply lubricating jelly in this manner.

This particular feature highlights another advantage of the "compartmentalized" structure of various embodiments of the invention. As the tray 100 includes multiple compartments, various tasks associated with a catheterization procedure can be completed while keeping the catheter within the tray 100. The ability to keep the catheter in the tray 100 reduces the risk that the catheter or corresponding devices will be contaminated with bacteria or microbes on other objects within the procedure room. For example, when the first compartment 101 is used to apply lubricating jelly to the catheter, the lubricating jelly can be applied while the catheter is contained within the tray 100, thereby reducing the risk that the catheter will become contaminated. This correspondingly reduces the risk of infection for the patient receiving the catheter.

Prior art systems, for example such as those in which the catheterization procedure components are shipped in separate containers, may contribute to substandard techniques in that the catheter can become contaminated when moving it from its shipping container. Consequently, the patient can be at an elevated risk of infection as the catheter is moved from one tray to another. Embodiments of the present invention solve this problem by providing a single level tray 100 with compartments. Further, in one embodiment the first compartment 101 includes the first opening 121 so the catheter can stay in place during and after lubrication. By having easy access to the components disposed in the single level tray 100, the medical services provider can more easily prepare and use the components within the tray 100. This helps to minimize the risk of contaminating the patient or the sterile field during the procedure.

In one embodiment, the second step portion 117 is configured to be inclined at a shallower angle than the first step portion 116 in at least a portion opposite the recess 119 from the first opening 121. When configured in such a fashion, the second step portion 117 includes a "cutdown" so that the catheter can stay within the channel both during and after lubrication.

Additionally, the catheter can be placed in both the first opening 121 and second opening 122 during lubrication. When positioned in this configuration, the second opening 122 helps to align the catheter with the first opening for easy passage through the lubrication channel formed by the second step portion 117.

The tray 100 of FIGS. 1-6 includes additional advantages over prior art catheter packaging as well. For example, in one embodiment, instructions 132 or other graphical indicia can be printed, placed upon, or molded into the horizontal flange 111. In one embodiment, compartment designations can be placed above each compartment to ensure the medical services provider uses the correct device or material at the correct time. In another embodiment, expiratory dates for materials or devices disposed within the tray 100 may be placed on the horizontal flange 111. It will be obvious to those of ordinary skill in the art having the benefit of this disclosure that the invention is not so limited. Any number of various text or picture combinations can be printed on, placed upon, or molded into various parts of the tray. For instance, graphical indicia can be applied to the compartment base members in addition to the horizontal flange 111. Note that the horizontal flanges, in one embodiment, can terminate in downwardly protruding vertical flanges for increased stability during the printing process.

Another advantage of the tray 100 is that its compartmentalized configuration helps to reduce the risk of contaminating a patient or compromising the sterile nature of the components stored in the tray 100. Since both the catheter assembly and medical devices corresponding to catheter use are stored within the same tray 100, the risk of cross-contamination between sterile work areas and non-sterile spaces is minimized. Further, by having the catheter assembly and the devices corresponding to catheter use stowed in a one-level tray rather than a multi-level, stacked configuration, the medical services provider can more easily prepare and use the catheter and corresponding devices disposed within the tray 100.

Figure 7:
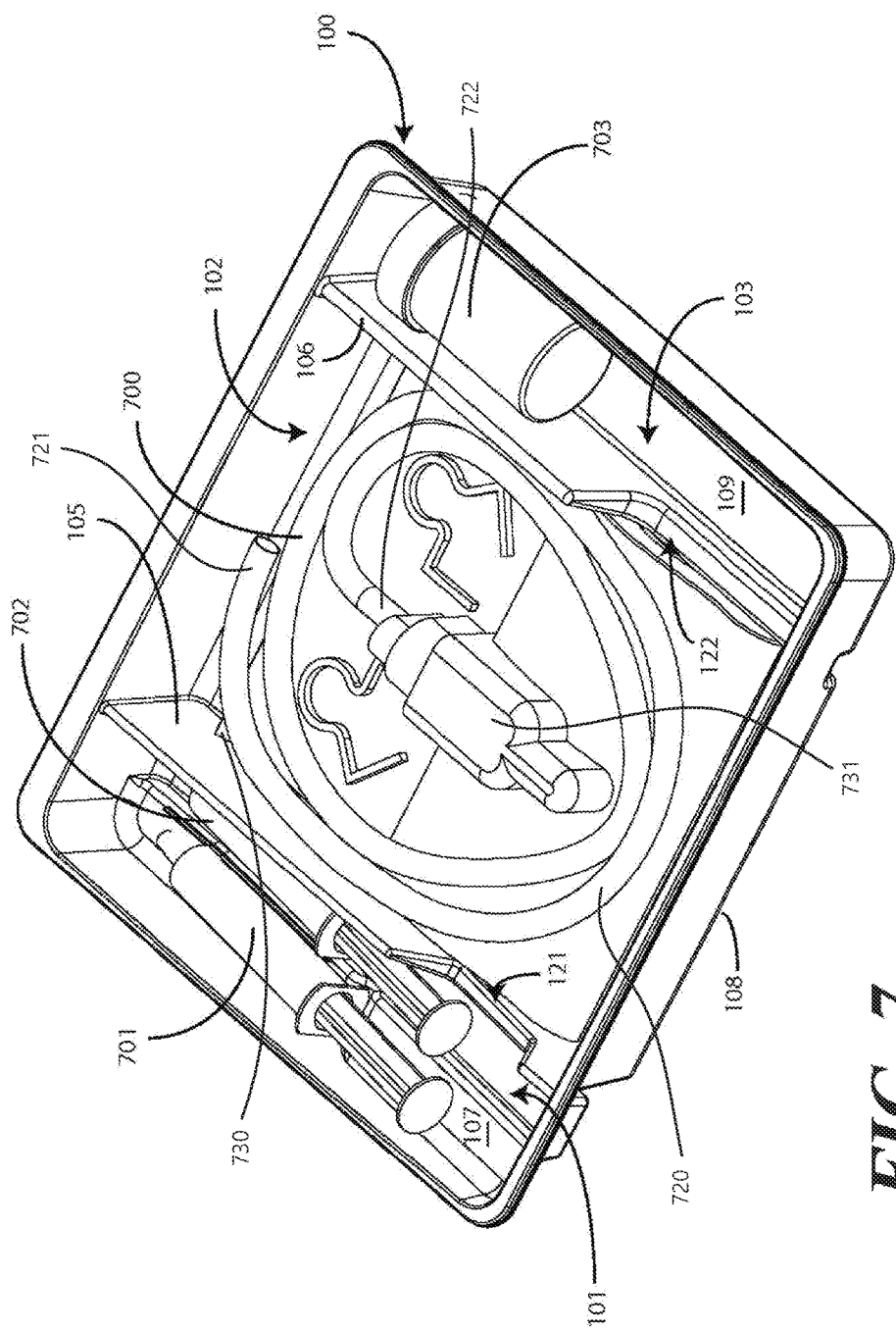
FIG. 7 illustrates a top, front, right perspective view of one embodiment of a tray for a catheter or similar assembly, with a catheter and corresponding procedural devices disposed therein, in accordance with embodiments of the invention.
Figure 8:
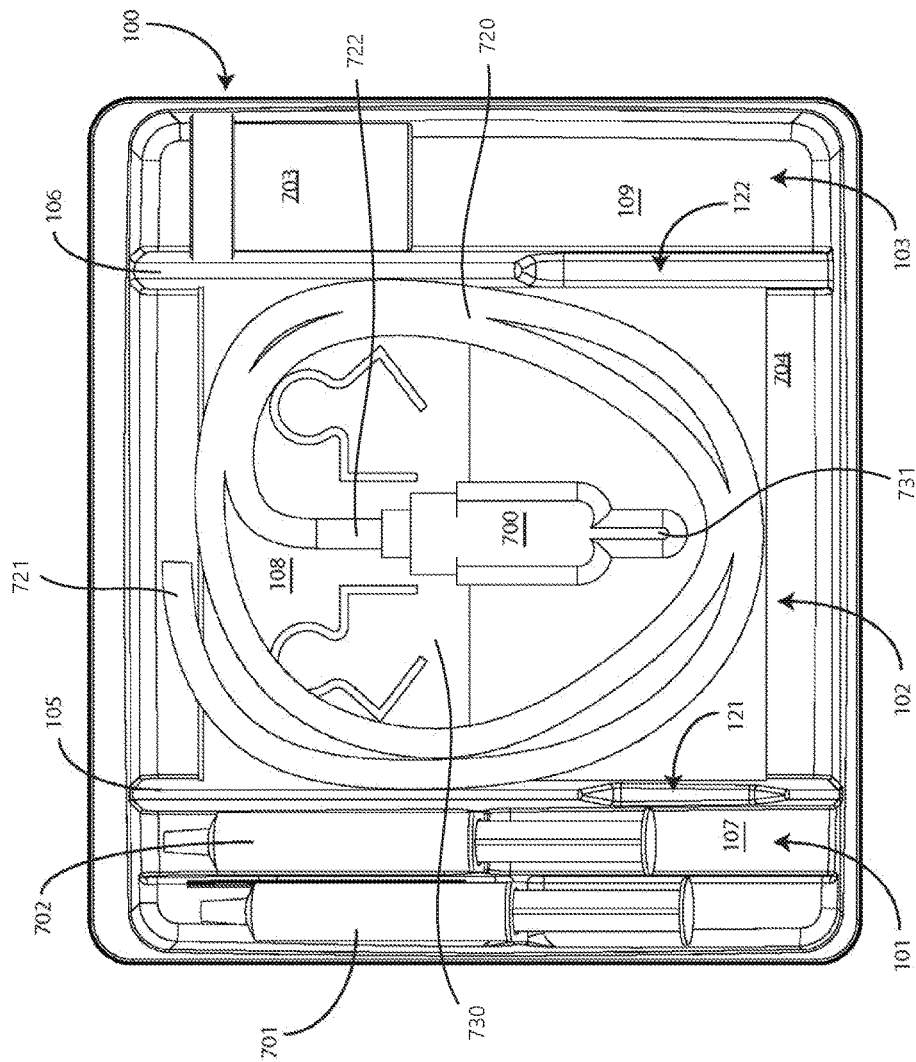
FIG. 8 illustrates a top plan view of one embodiment of a tray for a catheter or similar assembly, with a catheter and corresponding procedural devices disposed therein, in accordance with embodiments of the invention.
Figure 9:
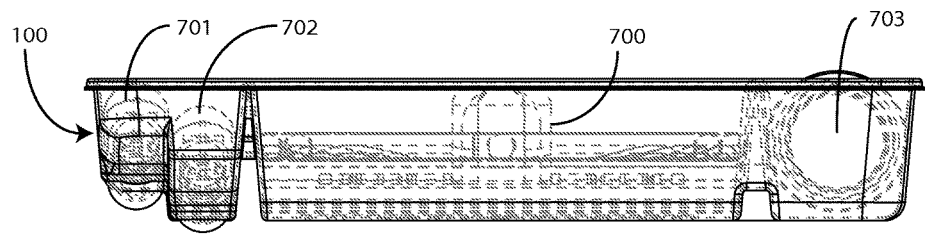
FIG. 9 illustrates a transparent, front elevation view of one embodiment of a tray for a catheter or similar assembly, with a catheter and corresponding procedural devices disposed therein, in accordance with embodiments of the invention.

Turning now to FIGS. 7-9, illustrated therein is a tray having a catheter assembly 700, syringes 701,702, and a specimen container 703 stored therein as a catheter packaging system in accordance with one embodiment of the invention. As with FIGS. 1-6, FIGS. 7-9 will be referred to collectively with like reference numerals referring to identical or functionally similar elements throughout the separate views. FIG. 7 illustrates a top, front, right perspective view of the catheter packaging system, while FIG. 8 illustrates a top plan view of the catheter packaging system. FIG. 9 illustrates a transparent, front elevation view of the catheter packaging system.

The illustrative catheter packaging system of FIGS. 7-9 includes a tray 100 having a first compartment 101, a second compartment 102, and a third compartment 103. In this illustrative embodiment, the first compartment 101 is configured to accommodate syringes 701,702. The second compartment 102 is configured to accommodate a coiled medical device, such as catheter assembly 700. The catheter assembly 700 includes an indwelling (or Foley) catheter coupled to a fluid bag 730 by a tube 720. The first end portion 721 of the tube 720 is coupled to the indwelling catheter and the second end portion 722 of the tube 720 is coupled to the fluid bag 730 via an anti-reflux device 731. The third compartment 103 is configured to accommodate the specimen container 703. The third compartment 103 can accommodate other materials as well, including skin sanitizers and cleansing liquids, solutions, or gels. As mentioned above, additional devices corresponding to catheter use, including towels, drapes, rubber gloves, and so forth, can be disposed in the tray 100 as well. As an illustration of this flexibility, a towel 704 is disposed beneath the catheter assembly 700.

As illustrated in FIGS. 1-6, each compartment of the tray 100 includes a compartment base member. Further, each compartment is separated by a barrier having an opening therein. A first barrier 105 having a first opening 121 therein separates the first compartment 101 from the second compartment 102. Similarly, a second barrier 106 having a second opening 122 therein separates the second compartment 102 from the third compartment.

Syringes 701,702 are disposed in the first compartment, with one syringe 701 being supported at a different elevation within the tray than the other syringe 702. The different elevations can be relative to each syringe 701,702, or to other components of the tray 100, such as the second compartment base member 108. Said differently, one syringe 701 is supported by the first compartment base member 107 at a shallower depth within the tray 100 than the depth of the second compartment base member 108. Further, where the first compartment base member 107 is inclined relative to other base members, one or both syringes 701,702 will be supported in a non-parallel configuration relative to the second compartment base member 108. This is most readily seen in FIG. 9.

As noted above, some medical procedures will call for more materials than can be accommodated by a syringe capable of fitting within the first compartment 101. For such procedures, the tray 100 can be packed with larger syringes. A large syringe (not shown) can be supported laterally within the tray 100 when it is placed across the tray 100 such that it lies within both the first opening 121 of the first barrier 105 and the second opening 122 of the second barrier 106. Such a syringe will pass across the top of the catheter assembly 700, but will be held in place by the side members of each opening.

Figure 10:
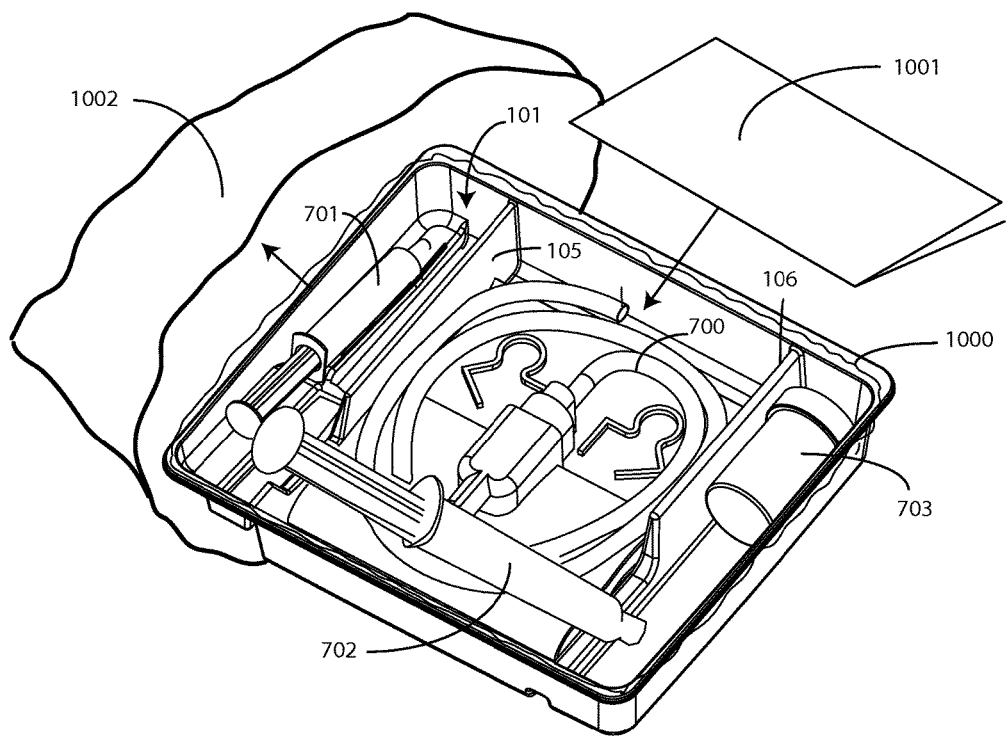
FIG. 10 illustrates a perspective view of one embodiment of a tray for a catheter or similar assembly, with a catheter and corresponding procedural devices disposed therein, along with instructions and packaging, in accordance with embodiments of the invention.

Turning now to FIG. 10, illustrated therein is an exploded view of the tray 100 having the catheter assembly 700, a pair of syringes 701,702, and a specimen container 703 disposed therein. In the configuration of FIG. 10, rather than having both syringes 701,702 disposed within the first compartment 101, one syringe 702 is disposed laterally in the first opening 121 and the second opening 122 of the first barrier 105 and second barrier 106, respectively.

Once the necessary components are disposed within the tray 100, the tray can be sealed with a CSR wrap 1000 to keep the internal components sterile. Printed instructions 1001 can then be attached or disposed upon the tray 100. In one embodiment, the printed instructions 1001 can tell the medical services provider how to perform a standard catheterization procedure. For instance, in one embodiment, the tray 100 is equipped with an adhesive label that can be used to identify the patient or specimen in the specimen container 703. Further, a label can be included to mark or otherwise identify the material in the fluid bag 730 attached to the catheter. Such labels can include pre-printed fields, such as date, time and name. Further the printed instructions 1001 can notify the medical services provider that the devices disposed within the tray 100 are ordered corresponding to use during the catheterization procedure.

In another embodiment, the printed instructions 1001 can inform the medical services provider of special instructions. For instance, in one embodiment the printed instructions 1001 can inform the medical services provider not to leave a catheter in a patient for more than forty-eight hours without a physician's approval. Where the printed instructions 1001 include such information, the labels included in the tray 100 may have pre-printed fields for the time of insertion that can be filled in by the medical services provider performing the catheterization procedure.

Once the printed instructions 1001 have been affixed to or placed with the tray 100, the assembly can be sealed in a sterile wrap 1002 such as a thermally sealed bag. Inclusion of a sterile wrap allows the instructions to be included with the tray assembly, yet outside the CSR wrap 1000. It will be clear to those of ordinary skill in the art having the benefit of this disclosure that the invention is not so limited, however. For example, the sterile wrap 1002 can be optional. Rather than including printed instructions 1001, the instructions for use can be printed on the CSR wrap 1000, thereby making the need for a sterile wrap optional.

Figure 11:
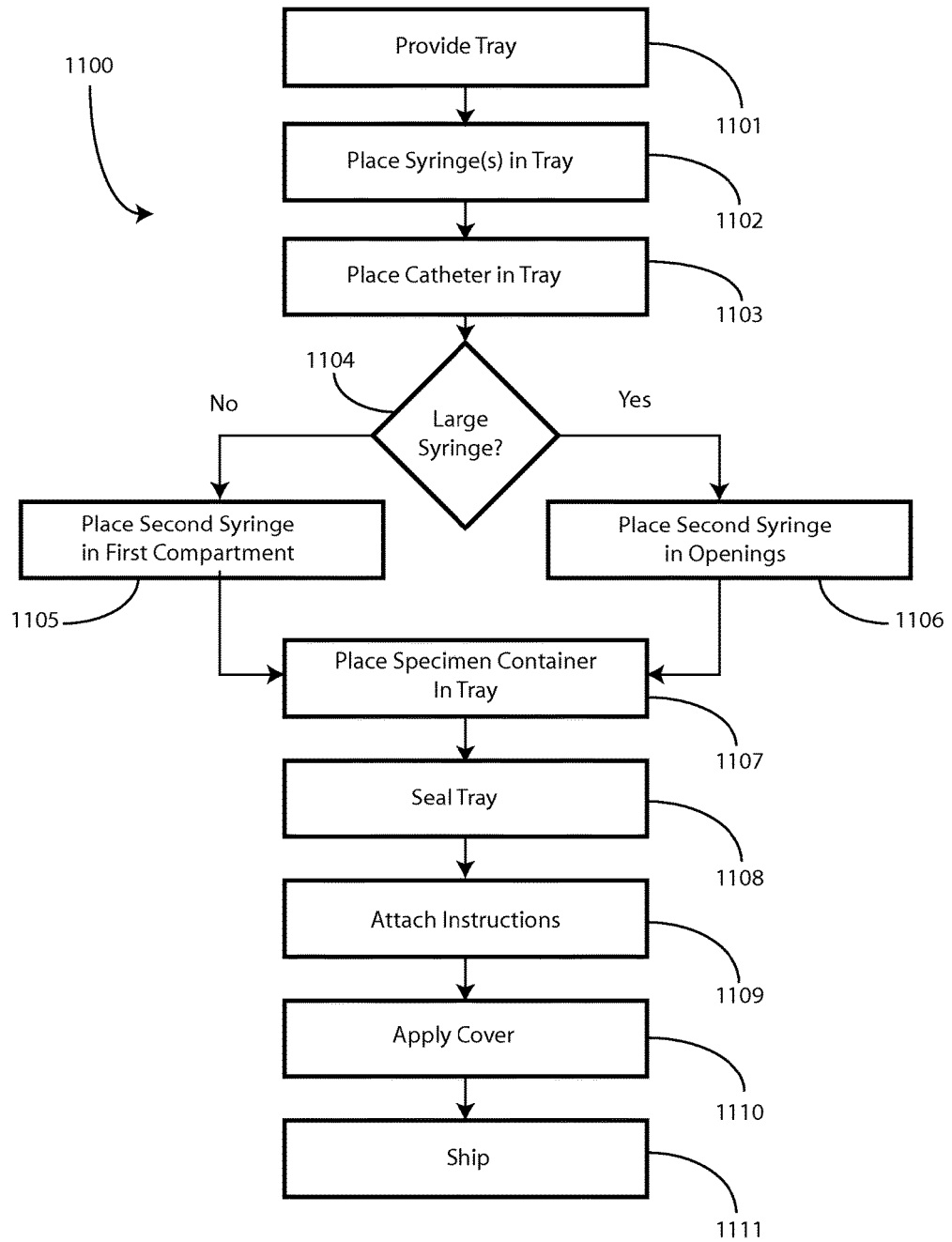
FIG. 11 illustrates a method of manufacturing one embodiment of a tray for a catheter or similar assembly, with a catheter and corresponding procedural devices disposed therein, in accordance with embodiments of the invention.

Turning now to FIG. 11, illustrated therein is a method 1100 for manufacturing a packaged catheter assembly in accordance with embodiments of the invention. At step 1101, the manufacturer provides a tray (100) having at least a first compartment (101) for accommodating one or more syringes (701,702) and a second compartment (102) for accommodating a flexible medical device, such as a catheter assembly (700). As noted above, in one embodiment the first compartment (101) will have a first compartment base member (107) having an inclined, stair-stepped contour (115). The first compartment (101) and second compartment (102) can be separated by a first barrier (105) having an opening (121) therein.

Once the tray (100) is procured, the manufacturer can dispose at least one syringe (701) in the first compartment (101) at step 1102. In one embodiment, as determined at decision 1104, a second syringe (702) will be disposed in the first compartment (101) at step 1105. In another embodiment, the second syringe (702) will be disposed laterally within the first opening (121) and, where present, a second opening (122) at step 1106.

At step 1103, the manufacturer will place the catheter assembly (700) in the second compartment (102). Other components may be disposed in the tray (100) as well, including a specimen container (703) in a third compartment (103) at step 1107, towels, drapes, printed instructions, and so forth.

At step 1108, the tray (100) is sealed. At optional step 1109, the manufacturer can enclose printed instructions (1001). In one embodiment, the printed instructions (1001) will direct a user to discharge contents of at least one syringe into the first compartment (101) and to pass at least a portion of the catheter assembly (700) through the opening and into the contents to lubricate the catheter.

At step 1110, the manufacturer can place a sterile wrap about the tray (100) and the printed instructions (1001), where included. At step 1111, the completed assembly can be shipped to a medical services provider.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A kit, comprising:
  a single level tray defining at least a first compartment and a second compartment, the first compartment bounded by a first compartment base member of the single level tray, the second compartment bounded by a second compartment base member of the single level tray, the single level tray including a barrier separating the first compartment from the second compartment, the barrier defining an opening;
  a first syringe containing an inflation fluid, the first syringe disposed within the first compartment of the single level tray;
  a second syringe containing a lubricant, the second syringe disposed within the single level tray, the first syringe and the second syringe configured for use during a catheterization procedure;
  an indwelling catheter; and
  a coiled tube coupling the indwelling catheter to a fluid receptacle, the indwelling catheter, the coiled tube, and the fluid receptacle disposed within the second compartment of the single level tray with the coiled tube being outside of the fluid receptacle, the opening of the barrier sized to receive a portion of the indwelling catheter when the indwelling catheter is passed from the second compartment into the first compartment to lubricate the indwelling catheter.

2. The kit of claim 1, wherein:
the first syringe and the second syringe are both within the first compartment; and
the single level tray defines a third compartment configured to accommodate at least one of a specimen container or a skin cleanser.

3. The kit of claim 1, wherein the second compartment base member and the first compartment base member are substantially coplanar.

4. The kit of claim 1, wherein the opening is bounded by an opening base member and two inclined opening side members.

5. The kit of claim 1, wherein each of the first compartment and the second compartment are accessible through a top opening defined by the single level tray, the top opening opposite the second compartment base member.

6. The kit of claim 1, wherein:
the indwelling catheter includes an inflatable portion configured to receive the inflation fluid from the first syringe to maintain the indwelling catheter within a patient.

7. The kit of claim 6, wherein each of the first syringe and the second syringe is contained within the single level tray at different depths within the single level tray.

8. The kit of claim 6, wherein the first compartment contains the first syringe at a shallower depth within the single level tray than the second syringe.

9. The kit of claim 1, further comprising printed instructions packaged with the single level tray, the printed instructions directing a user to discharge the lubricant from the second syringe into the first compartment.

10. The kit of claim 9, wherein the printed instructions further direct the user to pass at least a portion of the indwelling catheter into the first compartment, and through the lubricant discharged from the second syringe into the first compartment.

11. The kit of claim 1, wherein the single level tray defines a top opening through which the first compartment and the second compartment can be accessed, the kit further comprising:
a sterile wrap disposed about the single level tray covering at least the top opening.

12. The kit of claim 11, wherein when the sterile wrap is unwrapped from about the top opening such that at least the first syringe, the second syringe, and the indwelling catheter are revealed.

13. A kit, comprising:
a single level tray including a first compartment base member and a second compartment base member, the single level tray defining a first compartment and a second compartment, the first compartment base member forming a portion of a boundary of the first compartment, the second compartment base member forming a portion of a boundary of the second compartment, the single level tray including a barrier separating the first compartment from the second compartment;
a first syringe disposed within the first compartment of the single level tray, the first syringe containing an inflation fluid;
a second syringe disposed within the single level tray, the second syringe containing a lubricant; and
a catheter assembly including a coiled tube coupling an indwelling catheter to a fluid receptacle, the indwelling catheter including an inflatable portion configured to receive the inflation fluid from the first syringe to maintain the indwelling catheter within a patient, the fluid receptacle including an anti-reflux device, an end of the coiled tube coupled to the anti-reflux device, the coiled tube and the fluid receptacle disposed within the second compartment of the single level tray with at least a portion of the coiled tube being outside of the fluid receptacle and such that the fluid receptacle is between the second compartment base member and the coiled tube.

14. The kit of claim 13, wherein the coiled tube and the fluid receptacle are disposed within the second compartment of the single level tray with at least a portion of the fluid receptacle being beneath the coiled tube.

15. The kit of claim 13, wherein the barrier extends a length of the first compartment and defines an opening to receive a portion of the catheter assembly when a tip of the indwelling catheter is placed from the second compartment into the first compartment to lubricate the indwelling catheter.

16. The kit of claim 13, wherein the single level tray defines a top opening through which the first compartment and the second compartment can be accessed, the kit further comprising:
a sterile wrap disposed about the single level tray covering at least the top opening.

17. The kit of claim 16, wherein when the sterile wrap is unwrapped from about the top opening at least the first syringe, the second syringe, and the indwelling catheter are revealed.

18. A kit, comprising:
a single level tray defining a first compartment and a second compartment, the single level tray including a barrier separating the first compartment from the second compartment, the barrier extending a length of the first compartment and defining an opening;
a first syringe disposed within the first compartment of the single level tray, the first syringe containing an inflation fluid;
a second syringe disposed within the single level tray, the second syringe containing a lubricant; and
a catheter assembly including a coiled tube coupling an indwelling catheter to a fluid receptacle, the indwelling catheter including an inflatable portion configured to receive the inflation fluid from the first syringe to maintain the indwelling catheter within a patient, the coiled tube and the fluid receptacle disposed within the second compartment of the single level tray with at least a portion of the coiled tube being outside of the fluid receptacle, the opening defined by the barrier sized to receive a portion of the catheter assembly when a tip of the indwelling catheter is placed from the second compartment into the first compartment to lubricate the indwelling catheter.

19. The kit of claim 18, wherein the fluid receptacle includes an anti-reflux device, an end of the coiled tube coupled to the anti-reflux device.

20. The kit of claim 19, wherein:
the single level tray includes a first compartment base member and a second compartment base member, the first compartment base member forming a portion of a boundary of the first compartment, the second compartment base member forming a portion of a boundary of the second compartment; and
the coiled tube and the fluid receptacle are disposed within the second compartment of the single level tray such that the fluid receptacle is between the second compartment base member and the coiled tube.

21. The kit of claim 18, wherein the single level tray defines a top opening through which the first compartment and the second compartment can be accessed, the kit further comprising:
 a sterile wrap disposed about the single level tray covering at least the top opening.

22. The kit of claim 21, wherein when the sterile wrap is unwrapped from about the top opening at least the first syringe, the second syringe, and the indwelling catheter are revealed.

* * * * *

(12) INTER PARTES REVIEW CERTIFICATE (2189th)
United States Patent (10) Number: US 9,808,400 K1
Adler et al. (45) Certificate Issued: Jul. 7, 2021

(54) CATHETER TRAY, PACKAGING SYSTEM, AND ASSOCIATED METHODS

(71) Applicants: Deborah B. Adler; Alberto C. Savage; Earl D. Wilson; Jennifer E. Tomes; Jack E. Maze; Kenneth S. Chua; John Henry Kutsch

(72) Inventors: Deborah B. Adler; Alberto C. Savage; Earl D. Wilson; Jennifer E. Tomes; Jack E. Maze; Kenneth S. Chua; John Henry Kutsch

(73) Assignee: MEDLINE INDUSTRIES, INC.

Trial Number:

IPR2019-00208 filed Nov. 7, 2018

Inter Partes Review Certificate for:

Patent No.: 9,808,400
Issued: Nov. 7, 2017
Appl. No.: 14/265,909
Filed: Apr. 30, 2014

The results of IPR2019-00208 are reflected in this inter partes review certificate under 35 U.S.C. 318(b).

INTER PARTES REVIEW CERTIFICATE
U.S. Patent 9,808,400 K1
Trial No. IPR2019-00208
Certificate Issued Jul. 7, 2021

AS A RESULT OF THE INTER PARTES REVIEW PROCEEDING, IT HAS BEEN DETERMINED THAT:

Claims 13, 14, 16 and 17 are cancelled.

\* \* \* \* \*